(12) United States Patent
Chelala

(10) Patent No.: US 12,396,830 B2
(45) Date of Patent: Aug. 26, 2025

(54) METHOD FOR DESIGNING A PROSTHETIC ELEMENT

(71) Applicant: DENTAL DESIGN, Uccle (BE)

(72) Inventor: Pierre Chelala, Waterloo (BE)

(73) Assignee: DIGITAL DENTAL DESIGN ROBOTICS, Waterloo (BE)

( * ) Notice: Subject to any disclaimer, the term of this patent is extended or adjusted under 35 U.S.C. 154(b) by 1172 days.

(21) Appl. No.: 17/284,683

(22) PCT Filed: Oct. 15, 2019

(86) PCT No.: PCT/EP2019/077935
§ 371 (c)(1),
(2) Date: Apr. 12, 2021

(87) PCT Pub. No.: WO2020/078989
PCT Pub. Date: Apr. 23, 2020

(65) Prior Publication Data
US 2021/0369421 A1    Dec. 2, 2021

(30) Foreign Application Priority Data
Oct. 15, 2018  (EP) ..................... 18200412

(51) Int. Cl.
| G06G 7/48 | (2006.01) |
| A61B 6/51 | (2024.01) |
| A61C 1/08 | (2006.01) |
| A61C 9/00 | (2006.01) |
| A61C 13/00 | (2006.01) |
| A61C 13/34 | (2006.01) |

(52) U.S. Cl.
CPC .......... *A61C 13/0004* (2013.01); *A61B 6/512* (2024.01); *A61C 1/082* (2013.01); *A61C 9/0046* (2013.01); *A61C 13/34* (2013.01)

(58) Field of Classification Search
CPC . A61B 2034/2055; A61B 34/30; A61B 6/512; A61C 1/082; A61C 13/0004; A61C 13/34; A61C 5/77; A61C 9/0046
See application file for complete search history.

(56) References Cited

U.S. PATENT DOCUMENTS

| 9,318,308 | B2 | 4/2016 | Brown et al. |
| 11,753,681 | B2 | 9/2023 | Chiu et al. |
| 11,768,504 | B2 | 9/2023 | Ebrahimi Afrouzi et al. |
| 12,235,659 | B2 | 2/2025 | Ebrahimi Afrouzi et al. |
| 2009/0148816 | A1 | 6/2009 | Marshall et al. |

(Continued)

FOREIGN PATENT DOCUMENTS

| WO | 2018007935 A1 | 1/2018 |
| WO | 2018154485 A1 | 8/2018 |

OTHER PUBLICATIONS

Hwang, Jae Joon, et al. "Factors influencing superimposition error of 3D cephalometric landmarks by plane orientation method using 4 reference points: 4 point superimposition error regression model." PloS one 9.11 (2014): e110665. (Year: 2014).*

(Continued)

*Primary Examiner* — Nithya J. Moll
(74) *Attorney, Agent, or Firm* — CHRISTENSEN O'CONNOR JOHNSON KINDNESS PLLC

(57) ABSTRACT

A disclosed method for designing a prosthetic element is executable prior to a cutting of a tooth of a patient for placing the prosthetic element.

20 Claims, 7 Drawing Sheets

(56) References Cited

U.S. PATENT DOCUMENTS

| | | |
|---|---|---|
| 2012/0143364 A1 | 6/2012 | Mcleod et al. |
| 2013/0230827 A1 | 9/2013 | Kwon |
| 2015/0132718 A1* | 5/2015 | Kerschensteiner .... A61C 13/01 433/199.1 |
| 2015/0215584 A1 | 7/2015 | Tapia et al. |
| 2018/0071063 A1* | 3/2018 | Watzke ................ A61C 13/082 |
| 2018/0263726 A1 | 9/2018 | Fares et al. |
| 2023/0052634 A1 | 2/2023 | Tomblin et al. |
| 2023/0131624 A1 | 4/2023 | Tomblin et al. |
| 2023/0146701 A1 | 5/2023 | Tomblin et al. |

OTHER PUBLICATIONS

Written Opinion mailed Dec. 3, 2019, issued in corresponding International Application No. PCT/EP2019/077935, filed Oct. 15, 2019, 7 pages.

International Preliminary Report on Patentability mailed Apr. 14, 2021, issued in corresponding International Application No. PCT/EP2019/077935, filed Oct. 15, 2019, 9 pages.

International Search Report mailed Dec. 3, 2019, issued in corresponding International Application No. PCT/EP2019/077935, filed Oct. 15, 2019, 6 pages.

Written Opinion of the International Searching Authority mailed Dec. 3, 2019, issued in corresponding International Application No. PCT/EP2019/077935, filed Oct. 15, 2019, 8 pages.

Hogue, A. et al., "An optical-inertial tracking system for fully-enclosed VR displays," IEEE, 2004, 8 pages.

Huang, Haochong et al., "Infrared Digital Holography," IEEE Transactions on Instrumentation and Measurement, 2024, 37 pages, vol. 73.

Jans, Ryan M. et al., "Characterization of a Miniaturized IR Depth Sensor With a Programmable Region-of-Interest That Enables Hazard Mapping Applications," IEEE Sensors Journal, May 15, 2020, pp. 5213-5220, vol. 20, No. 10.

Patel, Kapil et al., "Simulation of a virtual reality tracking system," IEEE, 2011, 6 pages.

* cited by examiner

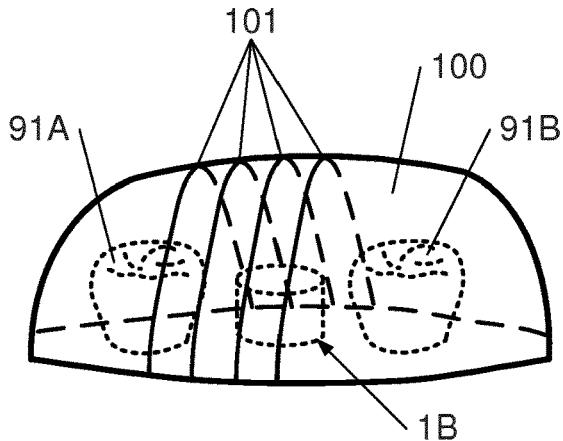
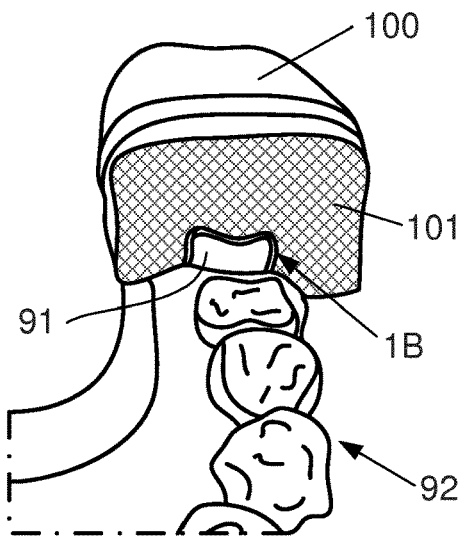
Fig. 5  Fig. 6
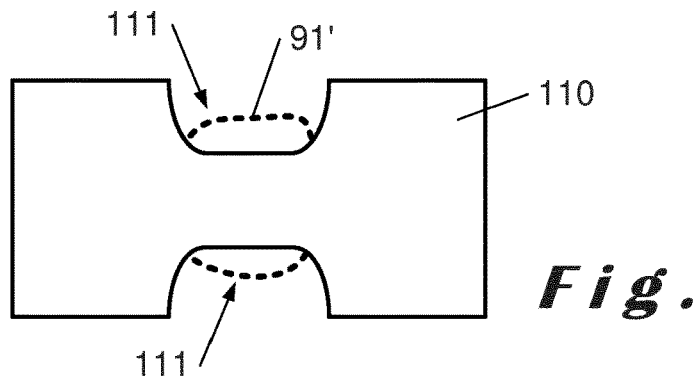
Fig. 7
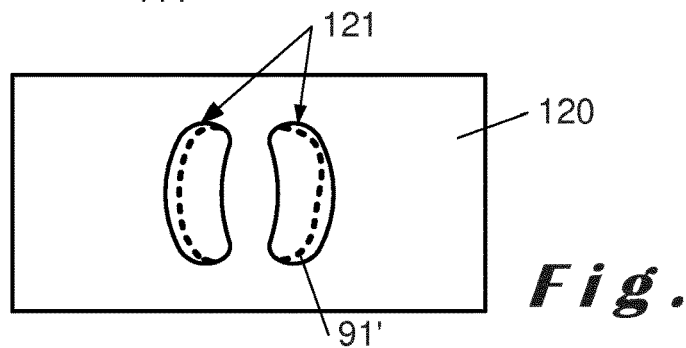
Fig. 8
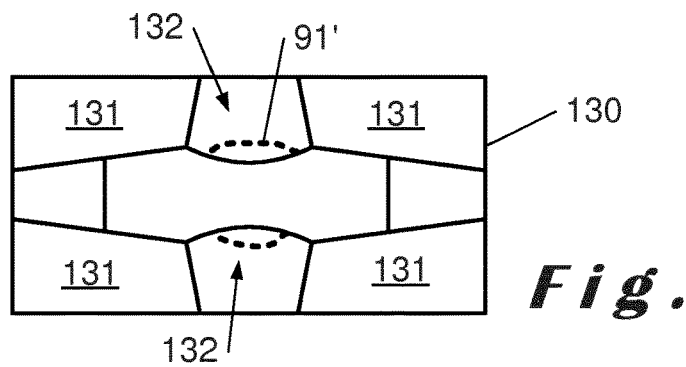
Fig. 9

METHOD FOR DESIGNING A PROSTHETIC ELEMENT

FIELD OF THE DISCLOSURE

The disclosure relates to a method for designing a prosthetic element.

BACKGROUND

Nowadays, when a dental restoration is to be carried out on a tooth of a patient via the placement of a prosthetic element, it is common practice for a dentist to proceed to a preparation of the tooth, comprising for example the following steps: cutting the tooth, followed by taking an impression of the cut tooth. This impression is sent to a laboratory for the design of the prosthetic element, which is then tested, adapted if necessary, and finally placed on the cut tooth of the patient.

Despite the advent of computerized methods for taking this impression digitally, the entire dental restoration process is long and requires a number of appointments of a patient to his dentist.

In addition, the cutting of the tooth by the dentist, the impression materials and the workflow in the laboratory are regular sources of technical errors that jeopardize the therapeutic effect expected from a dental restoration. In particular, it is complex for the dentist to take into account the overall structure of the hard and soft tissues associated with the dentition of the patient, so that the cutting is only rarely perfectly adapted both to the patient and to the technical constraints of the dental technician producing the prosthetic element.

SUMMARY

An object of the disclosure is to provide a method for designing a prosthetic element more adapted to the needs of a patient, allowing faster, cheaper and more reliable manufacture of the prosthetic element and treatment of the patient. For this purpose, the present disclosure provides a method for designing a prosthetic element comprising the following steps, performed in this order:

i. providing a first computer file comprising:
   an intra-oral three-dimensional representation of a dentition comprising at least one tooth to be restored by means of the prosthetic element;
   a radiographic image of the dentition;
   identifying common reference axes on the intra-oral three-dimensional representation and on the radiographic image;
   comparing the intra-oral three-dimensional representation with the radiographic image, this comparison sub-step comprising an overlay of the common reference axes;
ii. determining a three-dimensional representation of an extrados of the prosthetic element on the basis of the first computer file;
iii. determining technical parameters comprising:
   a dental protocol, and/or
   a type of dental preparation, and/or
   technical constraints,
   on the basis of the first computer file, at least one of the technical parameters being determined on the basis of the comparison sub-step of the step (i);
iv. generating a second computer file comprising a three-dimensional representation of a volumetric reduction of the at least one tooth on the basis of the technical parameters;
v. validating and/or modifying the second computer file;
vi. obtaining a three-dimensional representation of an intrados of the prosthetic element on the basis of the second validated and/or modified computer file;
vii. generating a third computer file comprising information relating to the three-dimensional representations of the extrados and intrados of the prosthetic element;
viii. producing the prosthetic element on the basis of the third computer file.

The method for designing a prosthetic element according to the disclosure makes it possible to implement a particularly efficient, inexpensive and rapid dental restoration process, providing a prosthetic element perfectly adapted to the needs of a patient.

Indeed, this method mainly concerns digital steps carried out prior to the dental restoration. In particular, the steps (ii) to (vii) are at the heart of the present disclosure, and are carried out by means of computer tools, in the background of the dental restoration. They make it possible to obtain a digital model of a prosthetic element which can be perfectly adapted to the needs of a patient without any cutting of the at least one tooth being necessary beforehand. The step (ii) essentially concerns the external aesthetics of the prosthetic element, the extrados of which is determined in correspondence with the first computer file, and thus globally with the dentition of the patient and the overall structure of the soft and hard tissues associated with this dentition. The steps (iii) to (vii) allow, among other things, to determine an intrados of the prosthetic element. This intrados must be perfectly adapted to a cutting of the at least one tooth. Nevertheless, in the case of the present disclosure, this cutting has preferably not been carried out in a concrete and real way beforehand, but preferably virtually, in the steps (iv) and (v), defined in the form of a volumetric reduction of the at least one tooth based on the information of the first computer file provided in the step (i) and on the parameters deduced from these information in the step (iii), preferably by a specialized computer scientist and/or an experienced dental technician. Thus, the intrados is determined a posteriori essentially on the basis of this volumetric reduction. The second modified and/or validated computer file containing the three-dimensional representation of the volumetric reduction therefore contains all the information necessary to carry out this volumetric reduction, which makes it possible to subsequently cut the at least one tooth so that its cut external surface corresponds exactly to the intrados of the prosthetic element. Thus, and very advantageously, it is possible to digitally define and produce the prosthetic element thanks to the design method according to the present disclosure, and, only afterwards, to cut the at least one tooth on the basis of the definition of the volumetric reduction of the at least one tooth contained in the second computer file after validation and/or modification. The prosthetic element produced is then more adapted to the needs of a patient, in particular to his dentition and the soft and hard tissues associated with it, as well as to the technical constraints, for example tolerances, of manufacturing a prosthetic element, than another prosthetic element which would be produced on the basis of an impression of the at least one tooth cut more approximately by the dentist.

In this context, the volumetric reduction (preferably defining a cutting) of the at least one tooth is therefore calculated before the intrados of the prosthetic element, although subsequently, in practice, it is the prosthetic element that is produced before (or at the same time as) the volumetric reduction.

In the next part of the summary, the steps of the design method according to the disclosure are commented on precisely. It is then presented different advantages of this method, particularly in the implementation of a dental restoration.

The step (i) advantageously provides a large amount of information about the dentition and the soft and hard tissues associated with this dentition to a dental technician and/or a CAD designer to define more precisely the needs of the patient, and thus a more suitable prosthetic element through the steps (ii) to (vii). It is proposed to provide one (or more) intra-oral three-dimensional representation of the preferably uncut dentition. This sub-step can be performed in less than 30 seconds using an intra-oral scanner known to a person skilled in the art. The radiographic image can be provided by any X-ray apparatus known to a person skilled in the art. It is preferably a two-dimensional image. Such an image is easier and cheaper to produce while providing sufficient relevant information for the comparison sub-step. A three-dimensional radiographic image (for example, produced by a conical beam computed tomography, or CBCT) is not, however, excluded from the scope of the disclosure. The images provided by this step (i) are preferably used to define very precisely a type of preparation and/or technical constraints in the step (iii), in particular thanks to the comparison sub-step.

Indeed, if it is counter-intuitive to overlay three-dimensional and two-dimensional data (for a two-dimensional radiographic image) this overlay is sufficient to identify, for example, the pulp chamber and the nervous system associated with the at least one tooth in order to take full account of it in the determination of the technical parameters in the step (iii). In particular, such a radiographic image is useful in the case of a dental restoration requiring re-cutting of a certain tooth, for example, in the case of a removal of an old prosthetic element. This makes it easier to identify the certain tooth and the associated soft and hard bodies.

The step (i) also comprises identification of the common reference axes on the intra-oral three-dimensional representation and on the radiographic image, and an overlay of the common reference axes in the comparison sub-step. These axes play an important role in the work of the dental technician and/or dentist as they enable the definition of a suitable digital working reference frame on the at least one tooth. In particular, they preferably comprise an insertion axis for the at least one tooth. It is therefore crucial that these axes are determined very precisely. The intra-oral three-dimensional representation is sufficient to determine such axes, but the radiographic image allows slight adaptation of these axes to take into account elements not visible on the radiographic image such as the pulp chamber and/or the nervous system associated with the at least one tooth. Thus, the comparison of the images by overlaying the axes provides an excellent basis for defining an ideal digital working reference frame for the subsequent steps of the method, while at the same time making it possible to detect technical constraints which would not be directly apparent on a single intra-oral three-dimensional representation. In general, the step (i) is very advantageous for the intelligent and accurate planning of a volumetric reduction (and hence a cutting) of the at least one tooth.

Optionally, the step (i) also comprises a step of providing an UV captured image and its overlaying and/or its comparison with other data from the first computer file to detect the presence of caries, decayed cavities and/or amalgams.

The steps (ii) to (vii) of the design method according to the present disclosure constitute intelligent planning and preparation steps prior to the successful completion of a dental restoration. Various software known to a person skilled in the art make it possible to simulate and/or manipulate a three-dimensional image of a restored dentition. It is possible to obtain a design of a probable extrados of a prosthetic element to restore the at least one tooth from such a simulation. However, this design output is superficial, as it does not indicate how a dental restoration should be made or how a prosthetic element should be produced. Furthermore, by its very purpose, this design does not take into account many protocols and tolerances for manufacturing a prosthetic element adapted to the needs of a patient. This is why the design method according to the disclosure proposes to study the first computer file in the step (i), in order to deduce the technical parameters of the step (iii). These technical parameters preferably comprise at least one of: information on the dentition, the dental roots, the gums, the periodontal tissue, a gingival index, teeth which are adjacent and/or antagonistic to the at least one tooth, information on teeth alignment and crowding, the mouth access zones, the nature of a design material of the prosthetic element as well as the tolerances associated with this material, and in particular the minimum wall thickness of the prosthetic element and/or parameters specific to a production center of the prosthetic element. These elements are preferably an integral part of a dental protocol determined directly and algorithmically from the step (i), and in particular therefore on the basis of the first computer file. Preferably, the step (i) makes it possible to determine a type of dental preparation (comprising, for example, the type of dental preparation to be carried out, the at least one tooth to be restored, the type of prosthetic element and the minimum thickness that it must have, etc.) and preferably also an insertion axis of the at least one tooth among the reference axes and/or numerical cutting axes among these reference axes, these data being provided as inputs for an algorithm advantageously making it possible to generate a dental protocol algorithmically on this basis. This is advantageously discussed later in this summary.

In this way, all the experience of a dental technician is put to use in the design of a prosthetic element, by the automatic establishment in the step (iv) of a plan for the volumetric reduction of the at least one tooth taking into account all these parameters. This automatic establishment is preferably carried out on the basis of a computer program especially advantageously designed within the scope of the present disclosure, preferably using a dental protocol as input. This step (iv) gives rise to the generation of the second computer file. The step (v) to validate and/or modify its content, and more specifically the three-dimensional representation of the volumetric reduction of the at least one tooth. Various parameters are thus preferably controlled by an authorized person, for example, a dental technician.

These steps (iv) and (v) are very advantageous because they allow for assistance in determining the parameters to be taken into account in order to virtually define a prosthetic element, while at the same time allowing a freedom to validate and/or modify this second computer file obtained. In particular, the second computer file is modifiable and is not the result of a closed software providing an automatic design of a non-exploitable prosthetic element.

Preferably, the second computer file is a modifiable CAD file, preferably in STL format, defining a virtual cutting of the at least one tooth based on the steps (i) to (iii), so that it constitutes a file which can be delivered from the step (iv), but also exploited and modified in the step (v) and in the subsequent steps. The step (v) preferably comprises a validation and/or a modification of each of the geometrical parameters relating to the three-dimensional representation of the volumetric reduction of the at least one tooth. Preferably, these geometrical parameters are among:
- peripheral margin lines,
- parallel planes bordering the lateral sides of the at least one tooth,
- a gingival outline of the at least one tooth,
- cutting axes of the at least one tooth,
- zones of volumetric reduction of the at least one tooth,
- volumetric reduction faces of the at least one tooth,
- volumetric reduction sizes for each of the volumetric reduction zones of the at least one tooth.

All of these parameters must be taken into account when designing a prosthetic element. More preferably, each of the geometrical parameters can be modified within a set of admissible values previously defined by at least one of the technical parameters determined in the step (iii), preferably by the dental protocol. In this way, an inexperienced or distracted technician would not make mistakes in the design of the prosthetic element.

The second computer file thus validated and/or modified therefore comprises a three-dimensional representation of the volumetric reduction of the at least one tooth, and can therefore serve as a basis for obtaining in the step (vi) a three-dimensional representation of the intrados of the prosthetic element, which is complementary to an external surface of the at least one volumetrically reduced tooth. The second computer file and all the representations thus defined of the intrados and the extrados of the prosthetic element are preferably CAD computer files known to a person skilled in the art but which can be advantageously exploited according to the disclosure. Once the design of the prosthetic element has been defined, a third computer file is then generated, preferably of the CAM type, containing information relating to these three-dimensional representations of the intrados and extrados defining the design of the prosthetic element. These information is used as the basis for the production of the prosthetic element in the step (viii) without losing the possibility of using the information of the second computer file to guide a practitioner in the cutting of the at least one tooth in order to correspond with the previously defined volumetric reduction.

This third computer file differs from the second computer file in that it comprises technical information that can be used directly during the production of the prosthetic element, in particular by a production machine, whereas the second computer file preferably comprises three-dimensional representation data. Obtaining the third computer file from the second one is not done using existing software but from a computer program according to the disclosure in order to again take into account the technical parameters, and preferably very specifically to take into account design protocols of the prosthetic element and dental protocols of dental machining. Preferably, the third computer file is also a CAM file, optionally stereolithography.

Very preferentially, the information of the third computer file comprises instructions for machining a material, and the step (viii) comprises a sub-step for machining the material based on the machining instructions. In this way, a machine tool configured to read the instructions can machine a material into a hollow shape with an inner face similar to the representation of the intrados and an outer shape similar to the representation of the extrados. The material preferably comprises at least one of ceramics, zirconia, hybrid ceramics, composite, resin, in order to design a strong and biocompatible prosthetic element, allowing the patient to benefit from a healthy, durable and stable dental restoration. Preferably, the material consists of bio ceramics suitable for machining.

Preferably, the step (ii) of the method comprises the following sub-steps:
- (ii.1) selecting a three-dimensional representation model of a model dentition from a database on the basis of the first computer file;
- (ii.2) selecting a zone of the three-dimensional representation model corresponding to a zone of the intra-oral three-dimensional representation corresponding to the at least one tooth;
- (ii.3) validating and/or modifying the zone of the three-dimensional representation model on the basis of the first computer file;
- (ii.4) defining the three-dimensional representation of the extrados of the prosthetic element from the validated and/or modified zone of the three-dimensional representation model.

This preferred implementation of the method essentially comprises a choice of a three-dimensional representation of a defect-free dentition simulating the three-dimensional representation of the dentition comprising the at least one tooth from a database (or library) of such representations. In this way, it is possible to determine a final shape of restored dentition adapted to the needs of a patient, and to derive the shape of an external envelope to be given to the prosthetic element to optimize the aesthetics of this new final shape of dentition. This external envelope basically consists of the extrados of the prosthetic element. Since no three-dimensional representation model may correspond exactly to the desired extrados, a validation and/or a modification step similar to that of the step (v) detailed above is planned to allow a dental technician and/or a CAD designer to make alterations to this zone. These may, for example, concern an insertion axis, an axis and/or a contact height of the at least one tooth with antagonistic and/or adjacent teeth, or a dental alignment. A gingival index is preferably taken into account to define the three-dimensional representation of the extrados.

In general, the design method according to the disclosure allows an inversion of an overall preparation step of the at least one tooth with a prosthetic element design, in an overall dental restoration process which then differs very advantageously from the prior art, in that it is considerably more efficient and faster. In particular, this dental restoration process offers a preparation of the at least one tooth comprising a cutting of the at least one tooth adapted to the prosthetic element and not the other way round. An example of a preferred embodiment such a dental restoration process using the design method according to the disclosure is described in the detailed description below. More specifically, the long sequence of appointments between the patient and the dentist can advantageously be replaced by a single appointment in which, on the one hand, the at least one tooth is cut by a dentist based on information from the second computer file and, on the other hand, the prosthetic element produced is placed on the at least one cut tooth. For example, if the prosthetic element is a crown of a tooth, this dental restoration can be performed in a single appointment lasting less than 30 minutes. The cutting of the at least one tooth based on the information from the second computer file is more accurate and precise, as it is based on rigorous information, studied and analyzed by one or more specialists, using reliable digital methods, far removed from the stressful working conditions of the dentist during a dental surgery operation. The compatibility between the cutting of the at least one tooth and the prosthetic element, on the one hand, and the overall structure of the tissues and the dentition, on the other hand, is thus assured and perfectly predictable. No impressions should be taken after the cutting of the at least one tooth, as it is assumed that the prosthetic element will be adapted to this cutting with a high accuracy, on the condition that this preparation is carried out on the basis of information from the second computer file.

Advantageously, the design method according to the disclosure thus makes it possible to avoid numerous return trips of the prosthetic element between a dental office and a laboratory where it is designed, such return trips being sometimes necessary according to the prior art for adaptations of the prosthetic element, when a test of placement of the prosthetic element on the tooth of the patient is not conclusive. In addition and advantageously, the design method according to the disclosure allows a large reduction in the suffering of a patient who has to undergo a dental restoration since the prosthetic element can be placed perfectly in a single session.

Advantageously, the design method according to the disclosure allows the production of prosthetic elements with the above-mentioned advantages at low cost for the patient because steps of dental impressions and/or possible modifications of the produced prosthetic element based on the cutting of the at least one tooth are no longer carried out. An advantageous reduction of this cost is estimated at one third of a design amount of the same prosthetic element by means of techniques according to the prior art. For a crown, this cost is estimated at €300. The overall cost of a dental restoration attributable to the production of a prosthetic element is therefore very significantly reduced, making dental restorations more democratic for a disadvantaged clientele.

The design method according to the disclosure, and the underlying dental restoration process advantageously respond to a growing societal need given the accelerated ageing of certain populations, particularly in Europe, the USA, Canada or Asia. The design method according to the disclosure makes it possible to quickly and efficiently produce high quality prosthetic elements that are perfectly adapted to the needs of each patient, thus meeting a growing demand for dental restoration while fully compensating for a shortage in nursing staff, particularly dental technicians or dental surgeons.

Advantageously, the design method according to the disclosure makes it possible to limit the ecological and environmental impact due to a relocation of a production of prosthetic elements. Indeed, it is possible to carry out the design method according to the disclosure locally, within a laboratory or a dental office, to produce prosthetic elements at low cost, without having recourse to cheap foreign labor. In addition, as the design method is primarily digital, a step can be added to verify compliance with safety and traceability standards specific to a prosthetic element.

An advantageous preferred embodiment of the disclosure is now presented, whereby the step (iii) comprises the following sub-steps:

(iii.1) determining a type of dental preparation on the basis of the first computer file;

(iii.2) algorithmically generating a dental protocol on the basis of the type of dental preparation determined in the step (iii.1), the dental protocol consisting of a collection of numerical data to geometrically parameterize the three-dimensional representation of the volumetric reduction;

(iii.3) validating and/or modifying the dental protocol on the basis of the comparison sub-step of the step (i).

This preferred embodiment of the step (iii) had been discussed above. It is based on a computer program which makes it possible to convert data on the type of dental preparation into an experimentally studied dental protocol so as to put all the inventor's experience at the service of the design of prosthetic elements. This embodiment makes it advantageously easy to carry out the step (iii) by minimizing the risks of an inexperienced dental technician making a mistake. A very precious time in the execution of the method according to the disclosure is thus saved. More precisely and more preferentially, the step (iii.1) comprises the following sub-steps:

visualizing the intra-oral three-dimensional representation of a dentition;

segmenting the intra-oral three-dimensional representation of a dentition so as to obtain an isolated three-dimensional representation of the at least one tooth;

algorithmically generate vestibular, lingual, mesial, distal and occlusal faces of the at least one tooth by identifying a point on each of these faces at the isolated three-dimensional representation of the at least one tooth;

modifying and/or validating boundaries of the vestibular, lingual, mesial, distal and occlusal faces of the at least one tooth (91) by adding, moving and/or removing points of these faces on the isolated three-dimensional representation of the at least one tooth;

identifying a reference frame of at least one of the reference axes on the basis of the comparison sub-step of the step (i), the reference frame comprising an insertion axis of the at least one tooth.

The type of dental preparation is thus determined with regard to digital manipulations of the intra-oral three-dimensional representation allowing the different faces of the tooth to be recognized and a working reference frame to be fixed on this three-dimensional representation. The practitioner can see by these digital manipulations and by means of the comparison sub-step of the step (i) (which has enabled advantageous detection of elements of the dentition, periodontal tissues, soft and hard tissues, nerves, etc.) the type of dental preparation (comprising volumetric reduction) that should be provided on the at least one tooth, and the working reference frame required to carry out this dental preparation. These embodiments allow a synergistic effect of the advantages of the steps (i) and (iii).

Preferably, following the segmentation sub-step, the interproximal periodontium is algorithmically taken into account in the dental protocol (by continuation according to a Bézier curve). This makes it possible, in the step (iv), to take into account gaps to be filled following this segmentation sub-step.

The dental protocol is preferably presented in the form of a table of real numbers corresponding to the numerical data which allow a geometrical parameterization of the volumetric reduction according to advantageous (indirect) relations which are an integral part of the disclosure. Preferably, the numerical data comprise:

for each face among the vestibular, lingual, mesial and distal faces of the at least one tooth:
  a radius;
  a height;
  corresponding to a parameterization of a transverse section of an elliptical (optionally circular) fillet of the face along an elliptical (optionally circular) arc of semi-major axis corresponding to the radius measured essentially perpendicularly to the insertion axis and semi-minor axis corresponding to the height measured essentially parallel to the insertion axis;
for each of the vestibular, lingual, mesial and distal faces of the at least one tooth:
  a first offset data corresponding to a displacement of each point of the face on the isolated three-dimensional representation of the at least one tooth towards the insertion axis;
for the occlusal face of the at least one tooth:
  a first offset data corresponding to a displacement of each point of the occlusal face on the isolated three-dimensional representation of the at least one tooth along the insertion axis;
  two percentages defining two zones consisting of marginal and middle zones of the at least one tooth on the isolated three-dimensional representation of the at least one tooth, each percentage corresponding to the ratio between a height of one zone and a height of the two zones (the latter preferably corresponding to a visible dental crown height, thus excluding the height of the dental root), these heights being measured essentially parallel to the insertion axis;
for each of the zones:
  a volumetric reduction orientation angle measured with respect to the insertion axis;
  a minimum height.

The insertion axis is known to a person skilled in the art. It is directed from the marginal zone to an occlusal face of the at least one tooth, or, in other words, from the root to the occlusal face of the at least one tooth, along the at least one tooth. The offset data preferably corresponds to a displacement towards the insertion axis of between 0.2 and 2.5 mm, more preferably between 0.4 mm and 1.5 mm, optionally about 1 mm. The radius and the height are preferably between 0.5 and 1.5 mm, optionally these data are about 0.9 mm and thus define a circular transverse section fillet on the vestibular, lingual, mesial and distal faces. Preferably the percentages are about 50%. The orientation angle for the marginal zone is preferably between 0 and 5°, preferably about 2°. Preferably, the angle of orientation for the middle zone is between 15 and 30°, preferably about 20°. Optionally, the minimum height associated with each zone is approximately 0.1 mm.

More preferentially, according to these embodiments of the disclosure, the technical constraints comprise a minimum thickness of a material for the design of the prosthetic element, and the first offset data of the faces depend on this minimum thickness. The minimum reduction that each face must undergo in order to be able to restore the at least one tooth by placing the prosthetic element is thus advantageously taken into account since the prosthetic element must have a certain minimum external wall thickness. It should be noted that this preferred embodiment is by no means limited to the case where the prosthetic element is a veneer, for example, intended to be placed on one of the faces, as in this case, approximately zero offset data can be provided for the other faces, which is logical since these data are generated algorithmically in the step (iii.2) depending on the type of dental preparation (i.e. a veneer).

Preferably, the first offset data are determined independently of the radii and the heights associated with the fillets. This is important because the first conical surface defined below in the step (iv.2) starts from an end curve bordering the elliptical fillets and a direct dependency of the first offset data would create breakpoints between the fillets and this first conical surface.

Advantageously and preferentially, these preferred embodiments of the step (iii) have a direct impact and application on the step (iv). Preferably, the latter comprises a sub-step of algorithmic generation of a three-dimensional representation of a volumetric reduction of the at least one tooth. This sub-step preferably comprises the following sub-steps (thus resulting advantageously from these preferred embodiments of the step (iii)):

(iv.1) generating a marginal surface consisting of the elliptical fillets of the vestibular, lingual, mesial and distal faces of the at least one tooth;

(iv.2) generating a first conical surface around the insertion axis from an end curve bordering the marginal surface generated in the sub-step (iv.1), this first conical surface extending parallel to the marginal zone and having an inclination towards the insertion axis of an angle corresponding to the volumetric reduction orientation angle of the marginal zone;

(iv.3) generating a second conical surface around the insertion axis from an end curve bordering the first conical surface generated in the sub-step (iv.2), this second conical surface extending parallel to the middle zone and having an inclination towards the insertion axis of an angle corresponding to the orientation angle of volumetric reduction of the middle zone;

(iv.4)
  calculating a second offset data for each point of the marginal and middle zones on the isolated three-dimensional representation of the at least one tooth, this second offset data corresponding to a displacement of this point towards or away from the insertion axis to displace this point on one of the first or second conical surfaces;
  defining a primary reduction surface by moving each point from the marginal and middle zones towards the insertion axis according to:
    the second offset data of this point if it corresponds to a displacement towards the insertion axis and if it is larger than the first offset data of this point,
    the first offset data of this point otherwise;

(iv.5) generating an occlusal surface from an end curve bordering the primary reduction surface generated in the sub-step (iv.4) by a displacement of each point on the occlusal face on the isolated three-dimensional representation of the at least one tooth along the insertion axis according to the first offset data;

(iv.6) smoothing and/or regularizing a total surface consisting of the assembly of the marginal, primary reduction and occlusal surfaces, this total surface having a plane tangent to the total surface at an intersection with the insertion axis perpendicular to the insertion axis.

This preferred embodiment of the step (iv) takes full advantage of the embodiments of the step (iii). Thus, the practitioner only needs to perform the step (iii.1) to algorithmically generate a three-dimensional representation of the volumetric reduction of the at least one tooth, thanks to the advantageous algorithmic steps (iii.2) and (iv.1) to (iv.6). Furthermore, it should be emphasized that this preferred embodiment of the step (iv) allows a volumetric reduction adapted to the type of dental preparation which goes far beyond a simple automatic volumetric removal per face. Indeed, the present disclosure is intended to provide a technical solution for the placement of a definitive prosthetic element and not a rough volumetric reduction for the placement of a temporary prosthetic element. It is thus proposed in this step (iv) to define two conical surfaces easy to design for a dentist for the successive volumetric reduction on the marginal and middle zones, and then to evaluate, in the sub-step (iv.4), that these conical surfaces are suitable for the placement of a prosthetic element according to the first offset data of the dental protocol. This operation is carried out point by point in an isolated three-dimensional representation. Thus, the primary reduction surface obtained in the step (iv.4) comprises both points on the conical surfaces and points determined by displacements according to the first offset data, so as to take into account both a subsequent simple and effective practice for the dentist and the entire dental protocol determined in the step (iii.3). This step represents a compromise between a dental cutting efficiency in order to obtain the desired volumetric reduction and the need to respect all the technical parameters determined in the step (iii), thus supporting the dental technician in his work in a remarkably advantageous way by means of algorithmic techniques developed within the scope of the disclosure.

The sub-step (iv.6) also plays an important role in smoothing and regularizing the various junctions between the conical surfaces, the other portions of the primary surface, the marginal surface and the occlusal surface, preferably proposing to flatten and/or truncate a region of the occlusal surface at its intersection with the insertion axis (so that the tangent plane is perpendicular to the insertion axis), thus avoiding any irregularity at this level, and facilitating both the design of the prosthetic element and the future volumetric reduction of the at least one tooth.

Preferably, the orientation angle for the marginal zone is between 0 and 5°. The first conical surface is therefore approximately cylindrical. Preferably, the orientation angle for the middle zone is between 15 and 30°. The second conical surface is therefore visually conical and its assembly with the first conical surface along the end curve bordering them forms a generally cylindrical-conical surface. The latter is attached to the marginal surface formed by the fillets of the vestibular, lingual, mesial and distal faces. This cylindrical-conical shape is very advantageous as it provides excellent anchorage and stability for the future prosthetic element, in particular preventing it from tilting. Thanks to the parameters of the dental protocol and the sequence of the steps (iv.1) to (iv.6), the volumetric reduction obtained from the cylindrical-conical shape is furthermore paramterized per face, which makes it possible to favor the aesthetics, the stability or the resistance of the future prosthetic element according to the face under consideration. For example, the aesthetics may be favored for a vestibular face, the stability for a lingual (or palatal) face, etc. This applies to other sub-steps. For example, for the occlusal face, the aesthetics and/or strength may also be given priority, in particular by providing sufficient space for the prosthetic element material. A volumetric reduction of the occlusal face should preferably be conical.

According to an embodiment of the design method, this method also comprises the additional step:
(vii') generating a fourth computer file on the basis of the second validated and/or modified computer file, the fourth computer file comprising machining instructions for the at least one tooth corresponding to the three-dimensional representation of the volumetric reduction of the at least one tooth.

This fourth computer file is preferably also a CAM (machining) file, generated on the basis of the second computer file in the same way as the third computer file is generated in the step (vii), but taking full account of the dental protocol for a cutting of the at least one tooth.

The fourth computer file has a great advantage over the second computer file in that it directly comprises machining instructions for the at least one tooth that can be used by a suitable machining machine and/or practitioner. This makes it easier to follow the machining instructions than to define a machining operation yourself from a CAD file for the volumetric reduction representation of the at least one tooth. This fourth computer file constitutes a major computer element of the disclosure because it proposes for the first time an exact machining of the at least one tooth, making it possible to obtain a machined external surface of the at least one tooth corresponding exactly to the intrados of the prosthetic element. This makes it possible to avoid a gap between the at least one cut tooth and the prosthetic element. The presence of such a gap would be detrimental to the dental integrity of the patient as it would allow bacteria to grow.

A preferred embodiment of the design method also comprises the following additional steps:
(vii") generating a fifth computer file on the basis of the second validated and/or modified computer file, the fifth computer file comprising information relating to the three-dimensional representation of the intrados of the prosthetic element obtained in the step (vi), this information comprising instructions for machining a rigid raw material corresponding to the three-dimensional representation of the intrados of the prosthetic element;
(viii") machining a block of the rigid raw material on the basis of the machining instructions of the fifth computer file, so as to produce a control key of a machining of the at least one tooth corresponding to a machining according to the three-dimensional representation of the volumetric reduction of the at least one tooth.

This fifth computer file is preferably also a CAM file, optionally of stereolithography or machining, generated on the basis of the second computer file in the same way as the third computer file is generated in the step (vii). This new file makes it possible to advantageously design a control key for the practitioner during the dental preparation. In fact, he can apply the control key to at least one tooth in order to check whether its cutting corresponds to the expected volumetric reduction (which defines the intrados of the prosthetic element). Although machining techniques are mentioned for the production of the control key, a production of this control key by three-dimensional printing techniques (and a reformulation of the steps (vii") and (viii") in this sense) would in no way depart from the scope of the disclosure. Preferably, depending on the embodiment comprising a production of a control key, the method also comprises the additional step of cutting the control key into slices parallelly to a plane. In this way, the practitioner can remove slices from the key so as to more easily see the correspondence between its cutting and the expected volumetric reduction by sectional view. These slices are preferably made horizontally (according to the occlusal surfaces of the teeth) or vertically (according to the insertion axis).

According to a preferred embodiment of the design method comprising the steps (iv.1) to (iv.6), it also comprises the following additional steps:

(iv') generating a sixth computer file on the basis of the first computer file and the dental protocol validated and/or modified in the step (iii.3), the sixth computer file comprising three collections of instructions for machining a rigid raw material, each of these collections comprising machining instructions for creating a cavity in the rigid raw material corresponding to the isolated three-dimensional representation, a first of the collections of instructions further comprising machining instructions for creating an access window at least partially conical around the cavity following the first and second conical surfaces, a second of the collections of instructions further comprising machining instructions for creating two windows of upper access to the cavity bordering mesial and distal faces of the cavity which correspond to the mesial and distal faces of the at least one tooth on the isolated three-dimensional representation, a third of the collections of instructions further comprising instructions for machining a portion of the rigid raw material surrounding a middle zone of the cavity corresponding to the middle zone of the at least one tooth on the isolated three-dimensional representation, to create two sloping edges according to the orientation angle of volumetric reduction of the middle zone;

(viii') machining a first, a second and a third block of the rigid raw material respectively based on the first, second and third collections of machining instructions of the sixth computer file, so as to produce three guides for machining the at least one tooth according to the three-dimensional representation of the volumetric reduction of the at least one tooth.

This sixth computer file is preferably also a CAM file, optionally stereolithography or machining. This new file makes it possible to advantageously design machining guides for the practitioner during dental preparation which are specifically adapted to allow the practitioner to reproduce the sub-steps of the step (iv) and thus obtain a (three-dimensional representation of the) volumetric reduction of the at least one tooth faithful to that validated and/or modified in the step (v). The machining guides obtained from the first, second and third blocks should preferably be used in this order so as to reproduce more or less directly certain sub-steps (or product of sub-steps) of the step (iv). Although machining techniques are mentioned for the production of the guides, a production of the guides by three-dimensional printing techniques (and a reformulation of the steps (iv') and (viii') in this sense) would in no way depart from the scope of the disclosure. The rigid raw material is preferably at least partly and/or at least locally transparent. Optionally, it is completely transparent. Optionally, it is at least partially colored. Preferably, it is transparent locally around the cavity to facilitate the visualization of the at least one tooth to be cut. Preferably, the guides also comprise reference markings comprising instructions for cutting the at least one tooth at least around the cavity. Preferably, depending on the embodiment comprising a production of the guides, the method also comprises the additional step of interlocking at least one safety abutment and a rail for positioning a dental drill on the first, second and third blocks. Thus, handling errors are avoided during the dental preparation thanks to the guides very advantageously provided in the scope of the disclosure.

In the context of this document, a "prosthetic element" preferably refers to one of the following element: a crown, a bridge, a filling, an inlay, an onlay, a dental implant, a veneer, or a combination of several of these elements. The term prosthetic element includes any type of fixed prosthesis, and any type of removable prosthesis partially or completely on at least one tooth and/or on at least one dental implant. Although a part of this document is particularly illustrated on the basis of a dental restoration comprising a design and/or a placing of a crown, a dental restoration by means of another prosthetic element cannot depart from the scope of the disclosure. In the context of this document, the terms "intrados" and "extrados" of a prosthetic element refer respectively to an inner surface and an outer surface of the prosthetic element, and are known to a person skilled in the art, a dental technician and/or a dentist.

In the context of this document, the terms "dentist", "dental surgeon", or more generally "practitioner" are preferably used interchangeably. The practitioner responsible for capturing an intra-oral three-dimensional representation and/or a radiographic image is preferably a dentist. The practitioner responsible for a cutting of the at least one tooth is preferably a dentist or a dental surgeon. A practitioner responsible for carrying out the steps (ii) to (vii) is preferably a dental technician who specializes in the digital design of prosthetic elements.

For the purposes of this document, the STL format is a computer file format known to a person skilled in the art. The abbreviation STL stands for Standard Triangle Language.

For the purposes of this document, a "fillet" is a clinical form of the cervical margin of a peripheral coronal preparation characterized by a slightly concave profile with an obtuse angle of connection between the prepared coronal zone and the unprepared zone.

For the purposes of this document, the at least one tooth is optionally a tooth. In general, the method is applied successively to each tooth when there is more than one. The anatomy of the crown of a tooth is divided into five faces known to a person skilled in the art as:

the "occlusal" face, which is the face to be bitten on;
the "vestibular" face, which is the face on the outside, against the cheek;
the "lingual" face (sometimes called the "palatal" face for the upper teeth) which is the face facing the palate on the inside and/or which the tongue usually touches;
the "mesial" face, which is the face hidden between two teeth closest to the central axis of the dental arch;
the "distal" face which is the face hidden between two teeth furthest from the central axis of the dental arch.

The use in this document of the verb "comprise" in its variants, as well as its conjugations, can in no way exclude the presence of elements other than those mentioned. The use in this document of the indefinite article "a", or the defined article "the" to introduce an element does not exclude the presence of a plurality of such elements.

The disclosure also proposes a prosthetic element produced by the design method according to the disclosure. All the preferred embodiments and all the advantages of the design method according to the disclosure are transposed mutatis mutandis to the present prosthetic element. In particular, the prosthetic element preferably consists of a bio ceramic material to ensure a biological compatibility with the soft and hard tissues and the dentition of a patient, as well as a very long service life of the prosthetic element.

The disclosure also proposes a control key produced by the preferred embodiments of the design method comprising the step (viii"). All of the preferred embodiments as well as all of the advantages of these embodiments are transposed mutatis mutandis to the present machining control key. The disclosure also proposes three machining guides produced by the preferred embodiments of the design method comprising the step (viii'). All the preferred embodiments as well as all the advantages of these embodiments are transposed mutatis mutandis to the present guides. Preferably the control key and/or the guides are made of rigid resin, preferably transparent.

The disclosure also provides tools for implementing the design method according to the disclosure: a set of apparatus, computer programs and computer-readable media. These tools are detailed below.

The present disclosure proposes:
- a first computer program comprising first instructions which, when the first computer program is executed, lead to the implementation of the step (iv) of the design method according to the disclosure;
- a second computer program comprising second instructions which, when the second computer program is executed, lead to the implementation of the step (vii) of the design method according to the disclosure;
- a third computer program comprising third instructions which, when the third computer program is executed, lead to the implementation of the additional step (vii') of the design method according to a highly preferred embodiment of the disclosure;
- a fourth computer program comprising fourth instructions which, when the fourth computer program is executed, lead to the implementation of the additional step (vii") of the design method according to a preferred embodiment of the disclosure;
- a fifth computer program comprising fifth instructions which, when the fifth computer program is executed, lead to the implementation of the additional step (iv') of the design method according to a preferred embodiment of the disclosure;
- a sixth computer program comprising sixth instructions which, when the sixth computer program is executed, lead to the implementation of the additional step (iii.2) of the design method according to a preferred embodiment of the disclosure.

The disclosure also provides a set of computer programs comprising the first and/or the second and/or the third and/or the fourth and/or the fifth and/or the sixth computer program. The disclosure also provides a computer-readable medium on which is recorded at least one computer program present in a set of computer programs according to the disclosure.

As detailed above, the first, second, third, fourth, fifth and sixth computer programs are at the heart of the design method according to the disclosure. They make it possible to partially automate the design of a prosthetic element, to digitally assist a dental technician in defining the prosthetic element, and to intelligently plan its production. In particular, the embodiments associated with these programs as mentioned above and the advantages of the associated steps (iii), (iv), (iv'), (vii), (vii') and (vii") are transposed to the programs and sets of programs, as well as to the computer-readable medium.

The present disclosure provides a set of apparatus for designing a prosthetic element by carrying out the design method according to the disclosure, the set of apparatus comprising:
- at least one imaging apparatus for providing the first computer file of the step (i) of the design method;
- a computer system comprising:
  - an interface for receiving:
    - at least one technical parameter determined in the step (iii) of the design method, and
    - validations and/or modifications of the second computer file of the step (v) of the design method;
  - and to visualize and/or communicate data on:
    - the intra-oral three-dimensional representation and the radiographic image of the first computer file (11) provided in the step (i); and on the three-dimensional representations:
    - of the extrados of the prosthetic element obtained in the step (ii);
    - the volumetric reduction of the at least one tooth of the second computer file generated in the step (iv);
    - the volumetric reduction of the at least one tooth of the second computer file validated and/or modified in the step (v);
    - the intrados of the prosthetic element obtained in the step (vi);
  - a logic unit for at least partially implementing the steps (ii), (iv), (vi) and (vii) of the design method;
  - a production machine for reading the information from the third computer file generated in the step (vii), and for implementing the step (viii) of the design method.

It is clear that various advantages and preferred embodiments of the set of apparatus according to the disclosure can be deduced directly from the set of preferred embodiments and the set of advantages of the design method according to the disclosure. In particular, the at least one imaging apparatus preferably comprises at least one of: an intra-oral scanner and an X-ray radiography apparatus. Preferably, the information in the third computer file comprises instructions for machining a material and the production machine comprises a machining machine for reading the third computer file and executing these instructions. Such a machining machine is known to a person skilled in the art, and the provision of instructions in a compatible computer file is the purpose of the step (vii). Preferably, the machine tool is configured to design several prosthetic elements simultaneously. Preferably, the computer system comprises a computer of which a screen, a keyboard and a mouse are the interface and of which the processor and at least one readable medium on which at least one of the first, second and/or third computer programs is recorded define the logic unit. For the appropriate embodiments of the disclosure, the logic unit is preferably also suitable for implementing the sub-step (iii.2) and the steps (iv'), (vii') and (vii").

The present disclosure provides a computer-readable medium on which a second computer file generated in the step (iv) and/or validated and/or modified in the step (v) of the design method according to the disclosure is recorded. The present disclosure also provides a computer-readable medium on which is recorded at least one of a third computer file being generated in the step (vii) of the design method according to the disclosure, and/or a fourth computer file being generated in the step (vii') of the preferred embodiment of the design method according to the disclosure.

The advantages and preferred embodiments of these steps (iv), (v), (vii) and (vii'), as well as of the second, third and fourth computer files, shall apply mutatis mutandis to the present computer-readable media. Preferably, the computer-readable medium on which the third computer file is recorded allow a physical transfer of the third computer file from a computer data center comprising a computer system as referred to above for the implementation of the steps (ii) to (vii), and (vii') of the design method, to a laboratory comprising a production machine for reading this third computer file and producing the prosthetic element. Preferably, the computer-readable medium on which the fourth computer file is recorded allows a physical transfer of the fourth computer file from the computer data center to a dental office or a medical center where a dentist will be able to read it by computer in order to find out the machining instructions for the at least one tooth to be executed.

The present disclosure also provides a computer-readable medium on which is recorded at least one of a fifth computer file being generated in the step (vii") of the design method according to the disclosure, and/or a sixth computer file being generated in the step (iv') of the preferred embodiment of the design method according to the disclosure.

The advantages and preferred embodiments of these steps (iv') and (vii"), as well as of the fifth and sixth computer files, shall apply mutatis mutandis to the present computer-readable media. Preferably, this computer-readable medium allows a physical transfer of the fifth and/or sixth computer files from a computer data center comprising a computer system as referred to above for the implementation of the steps (ii) to (vii), (iv') and (vii") of the design method, to an industrial zone comprising a production machine for reading this fifth and/or sixth computer file and producing the control key and/or the machining guides.

Below is now introduced an example of a system for assisting an operator in the placement of a prosthetic element designed by the design method, preferably making full use of the step (vii') of the method according to the disclosure. This system could be the subject of a disclosure as such independently of the disclosure which is currently claimed. The system for assisting an operator in a dental restoration which is proposed in this document comprises:
  a robot equipped with a mobile robotic arm and attached to a machining tool placed at one end of the robotic arm;
  a spatial guidance system for the robot comprising:
  a first spatial reference frame fixed to the robotic arm;
  a second spatial reference frame configured to be attached to one point in an operating zone;
  a detector configured to determine a first distance between the detector and the first spatial reference frame, and a second distance between the detector and the second spatial reference frame;
  a computer logic unit configured to:
  read a computer file comprising instructions for machining at least one tooth,
  receive data on first and second distances, and
  determine information for comparing the data with the machining instructions;
    a communication tool digitally connected to the computer unit to communicate the comparison information to the operator.

This assistance system allows advantageously an operator, preferably a dentist and/or a dental surgeon, to perform a cutting of the at least one tooth without technical errors.

Indeed, the communication tool allows to communicate to the operator comparison information determined by the computer logic unit between, on the one hand, machining instructions for the at least one tooth from a computer file and, on the other hand, a relative position between the robotic arm of the robot and an operating zone, via spatial reference frames from which a distance separating them is evaluated by means of the detector. In this way, deviations between the predetermined machining instructions and the actual machining action can be reported via a position of the robotic arm. The operator thus receives a report of his actions by means of the robot so that he can follow the machining instructions exactly and achieve a precise cutting without technical errors.

The guidance system is an essential component of the assistive system because without it, it is impossible to combine a robot action with a machining instruction, taking full account of possible variations in the position of the patient and a reference frame attached to the operating zone. Preferably, the guidance system can inform the operator and/or the robot in real time of a compensatory movement to be performed in relation to a movement of a patient, for example, due to breathing, jaw or mandibular movements.

Preferably, in general terms, an operating zone is defined as a small area of a mouth of a patient comprising at least one tooth to be restored.

Preferably, the robot is digitally connected to the computer logic unit, so that the latter is able to control an execution of the machining instructions by means of the machining tool. Thus, and very advantageously, the robot can proceed automatically to the cutting of the at least one tooth according to the machining instructions. However, the robot is preferably semi-automatic in the sense that it guides the operator through the execution of the cutting of the at least one tooth. In this way, it assists the operator, for example, by guiding the operator through a movement and/or rotation and/or vibration of the robotic arm, or by automatically stopping the machining tool if leaving the operating zone would be detrimental to the physical integrity of a patient.

Advantageously, the robot allows an unrivalled precision of around 20 microns for the operator alone, as well as a reduction in intervention time for the cutting of the at least one tooth of around 40 to 60%. Advantageously, the assistance system therefore allows the operator to carry out a cutting of the at least one tooth with great precision and without mental or physical fatigue. For the purposes of this document, the at least one tooth will optionally comprise at least ten teeth, and/or at least twenty-four teeth of a patient. The assistance system advantageously allows the operator to restore such a large number of teeth, in one session, without fatigue.

Preferably, the operator interacts with the robotic arm, in the sense that the robotic arm is also able to be guided to a certain extent by the operator, for example to be brought into the operating zone. The operator also has a preferred action of activating and deactivating the machining tool and/or the robot. In combination with the above preferred embodiment, the robotic arm can thus be brought into the operating zone by the operator and then work semi-autonomously under an execution control of the machining instructions by the computer logic unit. Advantageously, this double interaction of the robotic arm with the operator allows a high degree of flexibility, a safety and a precision for the operator in a dental restoration operation.

Preferably, the machining tool is a dental drill and the term machining refers to a milling.

Preferably, the robot comprises six bearings for partial rotation around six axes. It comprises wheels to move on the floor of a dental office.

The computer file in question preferably consists of a fourth computer file generated in the step (vii') according to the very preferred embodiment of the design method according to the disclosure.

In particular, in this case, the assistance system allows the operator to take into account the overall dentition and the hard and soft tissues of a patient, the cutting of the at least one tooth thus being perfectly adapted to the needs of the patient and to a prosthetic element previously designed by execution of the design method according to the disclosure. The assistance system thus makes it possible to implement a dental restoration process previously defined in this summary and from which the advantages are transposed to the present assistance system, the computer file is such a fourth computer file.

According to a preferred embodiment of the assistance system, the communication tool comprises a screen for displaying, at least partially, the operating zone and the machining tool in real time. Preferably, the comparison information also comprises a position and/or an orientation of the machining tool in the operating zone. Such a communication tool can be used to guide the operator through a dental preparation for a dental restoration, for example, by virtually guiding a manipulation to be performed on the screen or by offering several positions and/or orientations of the machining tool in the operating zone, or even several possible paths of the machining tool in the operating zone determined virtually via the computer logic unit on the basis of the computer file.

Optionally, the second spatial reference frame comprises at least one of:
an upper part comprising a helmet and/or at least one strap that can be placed around a forehead of a patient;
a lower part comprising a chin strap configured to enclose a chin of a patient;
and second target symbols detectable by the detector attached to the upper part and/or the lower part.

More optionally, the second spatial reference frame comprises the lower and upper parts. Advantageously, the second spatial reference frame allows an upper jaw and a lower jaw of a patient to be located individually. The upper part follows the movements of the upper jaw coupled to the forehead, while the lower part follows the movements of the lower jaw coupled to the chin. In addition, this second spatial reference frame can be advantageously used optionally for one class of patient.

Optionally, according to a new embodiment of the second spatial reference frame, it comprises a rigid patient's cheek retractor configured to force a rigidification of a mouth of a patient, allowing an access to the operating zone, comprising second target symbols on an upper and on a lower portion, these symbols being configured to detect by the detector. This new optional embodiment also allows an upper and lower jaws of the patient to be detected by the detector.

According to a preferred embodiment of the assistive system, the first spatial reference frame comprises first target symbols detectable by the detector; and the second spatial reference frame comprises:
a dental part configured to at least partially conform to a shape of a portion of a dentition within the operating zone;
a protruding element comprising second target symbols detectable by the detector, the protruding element being configured to be attached to the dental part by means of an attachment system so as to extend outside the operating zone.

Advantageously, such a second spatial reference frame allows the use of a dental part specific to the dentition of each patient, while the protruding element can be reused from one patient to another and attached by means of the attachment system to a dental part. A further advantage of the dental part is that it at least partially conforms to a shape of the portion of the dentition in the operating zone, so that the entire second spatial reference frame is more stable in relation to the reference frame of the patient, which is of primary importance for the purpose of the spatial guidance system of the robot. A second spatial reference frame of a different type, for example, based on target symbols that would be glued onto the teeth of the dentition, is also possible. However, the protruding feature of the protruding element is advantageous because this element extends outside the operating zone, making it easier for the detector to detect the second target symbols.

According to a special embodiment, the dental part is hemi-cylindrical in shape. The dental part then forms a significantly curved gutter that can be placed on the dentition.

Preferably, the dental part comprises a partial dental impression made from an intra-oral three-dimensional representation of the dentition, more preferably by means of an intra-oral scanner. More preferentially, according to the preferred embodiment for which the computer file is a fourth computer file obtained according to a step (vii') of the design method, the intra-oral three-dimensional representation is the one provided in the step (i). In view of the temporary use of the dental part, it may be made of a less resistant material than the prosthetic element, and for example, by means of machining techniques or additive manufacturing processes such as three-dimensional printing.

Independently of this semi-automated implementation, as mentioned above, the disclosure also offers devices to assist a dentist and/or a dental surgeon in the operation of cutting the at least one tooth by reducing the risk of technical errors. In this context, the practitioner is completely in control of the practice of the dental cutting, without any assistance from a robot, but he can nevertheless control and/or guide it by means of the control key and/or guides according to the disclosure.

DESCRIPTION OF DRAWINGS

Other characteristics and advantages of the present disclosure will appear when reading the following detailed description, for the understanding of which reference is made to the annexed figures among which:

FIG. 5 shows a three-dimensional view of a control key according to the disclosure;

FIG. 6 shows a three-dimensional view of a use of the control key illustrated in FIG. 5;

FIGS. 7 to 9 show a top view of the guides according to the disclosure;

Figure 1:
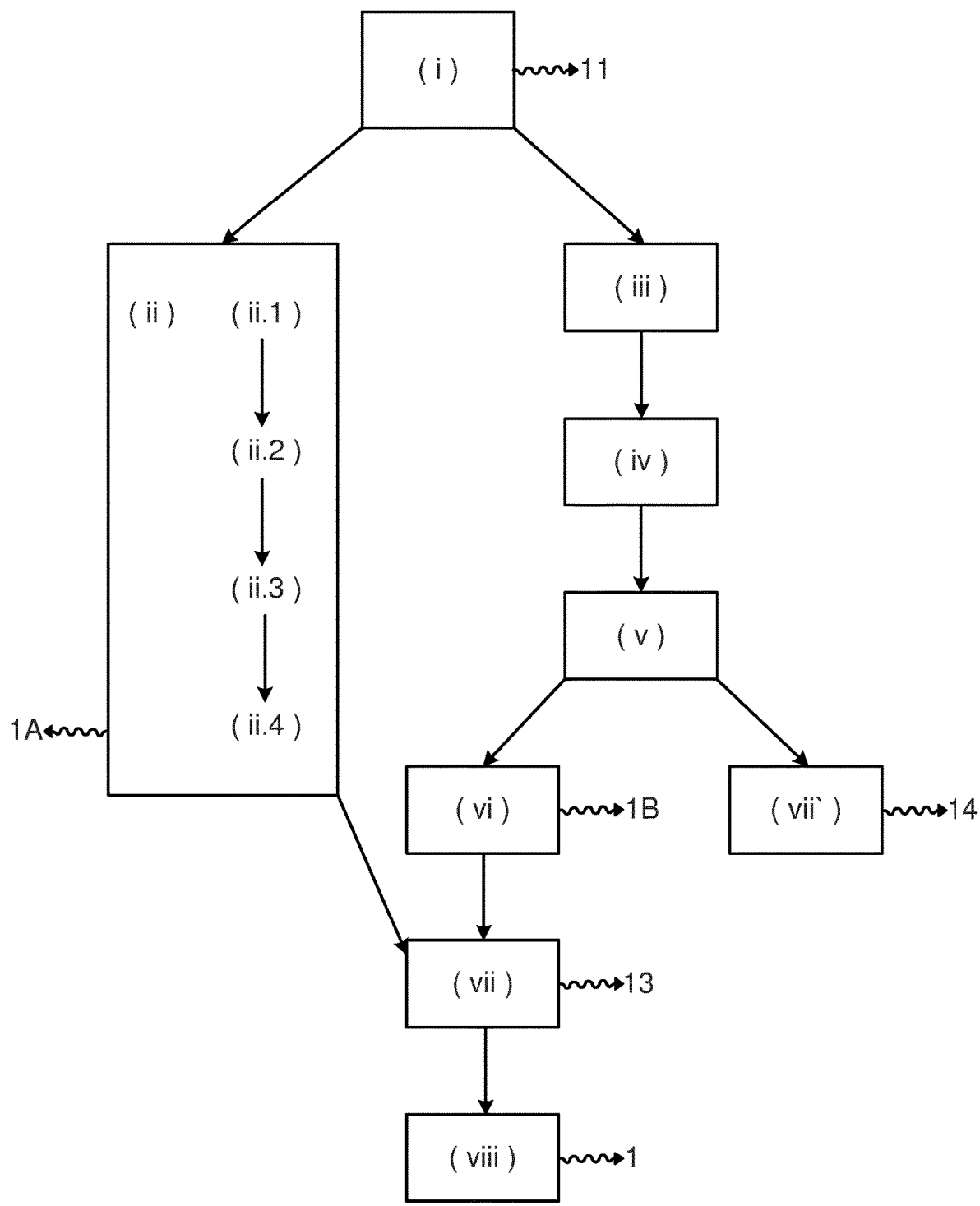
FIG. 1 shows a schematic view of a flow chart of a method for designing a prosthetic element according to a preferred embodiment of the disclosure.

The drawings of the figures are not to scale. Generally, similar features are denoted by similar references in the figures. In the context of this document, the identical or similar elements may have the same references. Furthermore, the presence of reference numbers or letters in the drawings cannot be considered as limiting, even where such these numbers or letters are indicated in the claims.

DETAILED DESCRIPTION

The present disclosure is described with particular achievements and references to figures but the disclosure is not limited by them. The drawings or figures described are only schematic and are not limiting.

Figure 2:
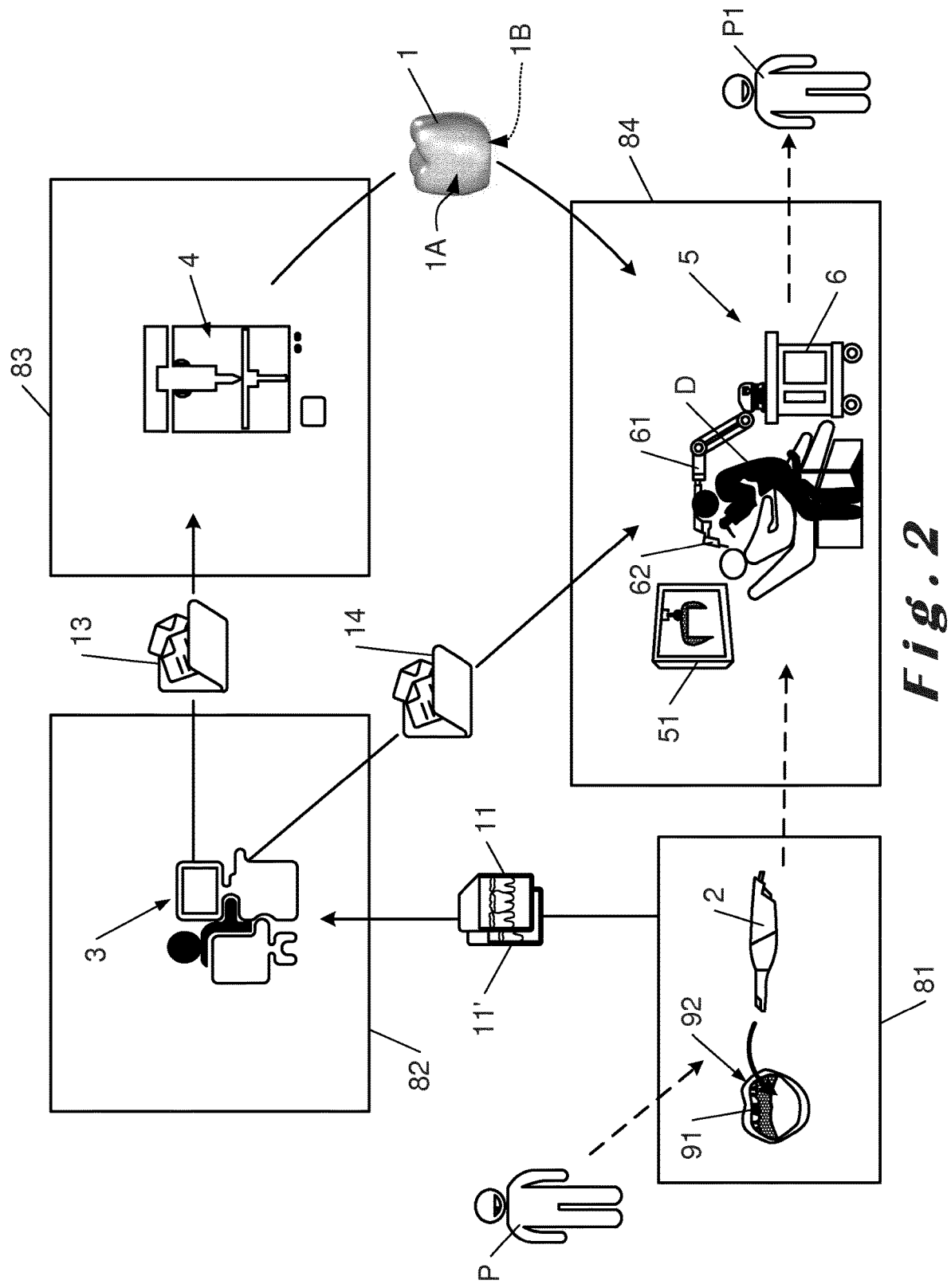
FIG. 2 shows a schematic view of an implementation of a dental restoration method comprising a method for designing a prosthetic element according to a preferred embodiment of the disclosure.

FIGS. 1 and 2 illustrate at least partially an implementation of a method of dental restoration of a tooth 91 of a dentition 92 of a patient P comprising a method for designing a prosthetic element 1 according to a preferred embodiment of the disclosure. Reference is hereafter made to the notations (i), (ii), (iii), . . . of the different steps of the design method introduced in the summary of the disclosure and in the claims.

It is assumed that the patient P is to undergo a dental restoration comprising milling of the tooth 91 and the placing of a prosthetic element consisting of a crown 1 on the milled tooth 91. The design method according to the disclosure is applied to the crown 1 to be designed. This method allows, according to a preferred embodiment, to be completed in such a way that the tooth 91 of the patient P can be restored easily and quickly.

To this end, the method proposes to the patient P to go to a three-dimensional imaging center 81 and undergo an intra-oral scan of his dentition 92 by means of an intra-oral scanner 2, in order to carry out the step (i), i.e., to provide a first computer file 11 comprising an intra-oral three-dimensional representation of the dentition 92 comprising the tooth 91 to be restored by means of the crown 1. The three-dimensional imaging center 81 is preferably one of: a dental office, a medical center, or a local imaging center. Advantageously, such a scan takes less than five minutes to complete; after this time, the patient P is released. It is preferably supplemented by a two-dimensional panoramic radiographic image of the mouth and/or the dentition 92 of the patient P, which is either attached to the first computer file 11, or provided simultaneously with the first computer file 11 in another first computer file 11'.

The panoramic radiographic image is preferably captured by means of an X-ray machine. It provides more information on the structure of the dentition 92 of the patient P, the associated nerves, the soft and hard tissues associated, comprising a comparison of the intra-oral three-dimensional representation with the radiographic image.

The first computer file 11 is then sent, via a computer-readable medium and/or via a shared data cloud, to a data center 82 comprising a computer system 3 allowing the steps (ii) to (vii), and (vii') of the design method to be carried out according to the preferred embodiment of the disclosure, in the order illustrated in FIG. 1, and as detailed in the summary of the disclosure. A dental technician and/or a specialized CAD designer processes the first computer file 11 to determine a representation of the crown 1, which comprises three-dimensional representations 1A and 1B of its extrados and intrados respectively, obtained from the steps (ii) and (vi) respectively. This representation is comprised in one or more computer files in STL format of CAD type designed at least partially by means of a first computer program according to the present disclosure. A second and a third computer program according to a preferred embodiment of the disclosure allows dental and prosthetic protocols to be used to generate a third 13 and a fourth 14 computer files of the CAM type which comprise instructions for machining respectively a ceramic material to form the crown 1, and the tooth 91 to fit the intrados 1B of the crown 1 during the placement.

The third computer file 13 is then sent, via a computer-readable medium and/or via a shared data cloud, to a laboratory 83 comprising a machining machine 4 allowing an implementation of the step (viii) of the design method according to the preferred embodiment of the disclosure. In particular, the machining machine 4 reads the third computer file 13 and executes the machining instructions so as to machine the ceramic material to form the crown 1, the extrados and the intrados of the crown 1 consisting of surfaces of a shape corresponding to the three-dimensional representations 1A and 1B.

The fourth computer file 14 is sent via a computer-readable medium and/or a shared data cloud to a dental office 84 of a dentist and/or surgeon practitioner D equipped with an assistance system 5 as described in the summary. It has to be noted that a practitioner D with such a machining machine 4 in the dental office 84 can receive the third computer file 13 and produce the crown 1 he needs himself. In particular, the locations 81, 83 and 84 are likely to coincide.

The practitioner D, having the fourth computer file 14 at his disposal, then carries out the dental restoration operation by milling the tooth 91 and attaching the crown 1 to the milled tooth. This operation is well known, but it can be significantly improved within the scope of the disclosure because the tooth 91 is milled with the help of the assistance system 5 described in the summary and in such a way as to fit into the already designed crown 1, and not the other way round. Thus, the operation lasts less than thirty minutes and the patient P regains a smile when leaving the dental office.

Figure 3:
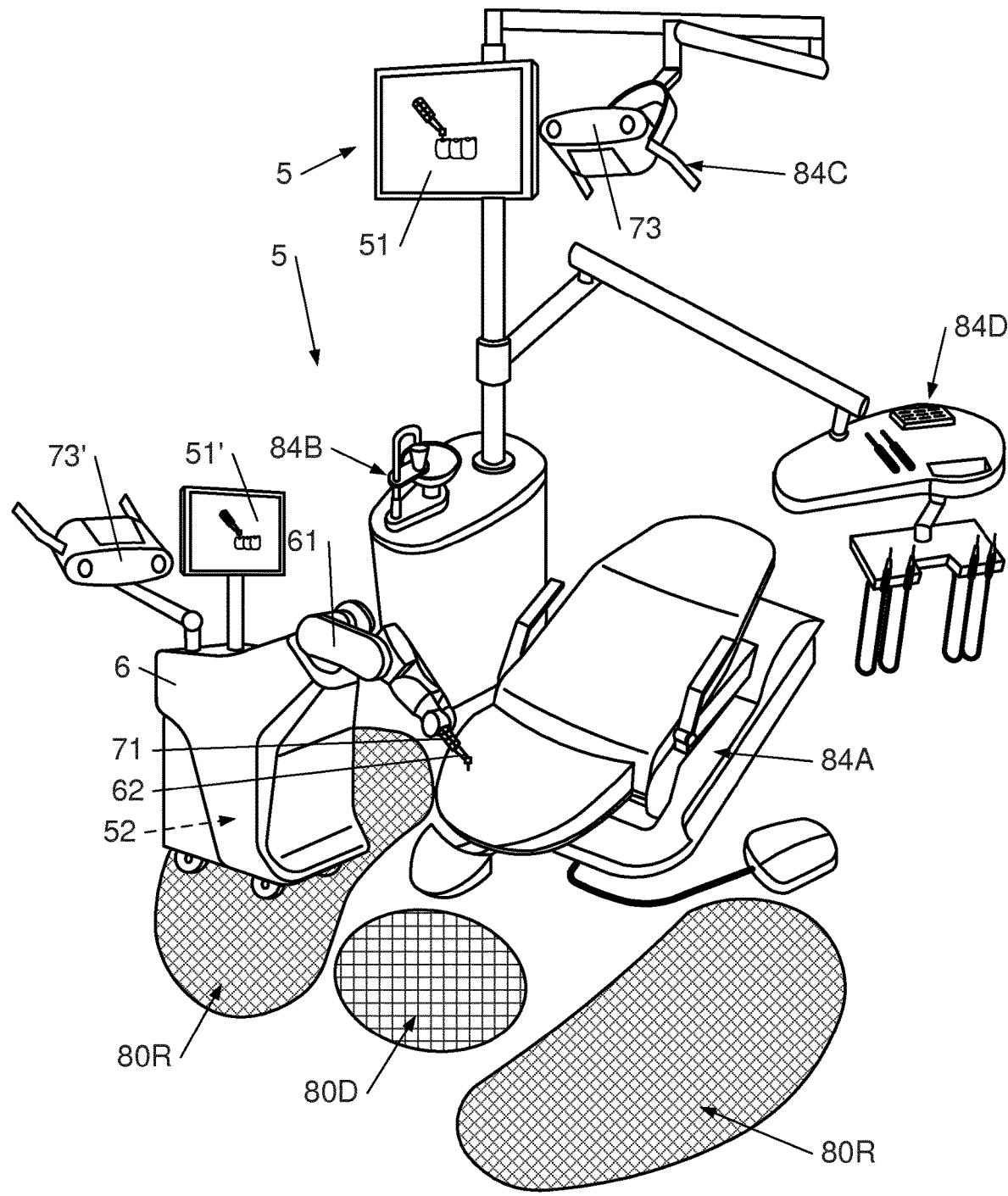
FIG. 3 shows a simplified perspective view of a dental office equipped with an operator assistance system in a dental restoration described in the summary.
Figure 4:
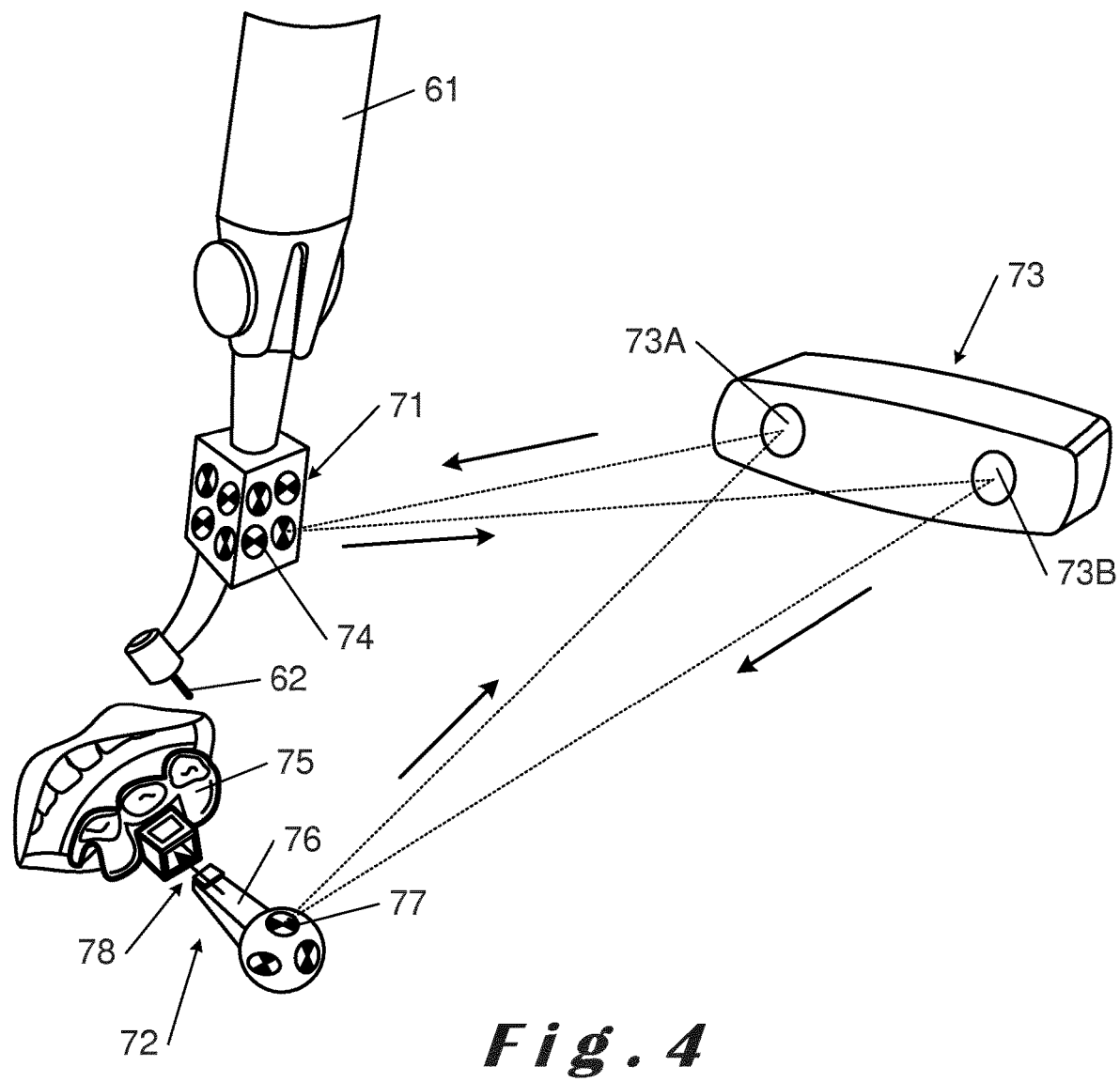
FIG. 4 shows a three-dimensional view of elements of a robot and a spatial guidance system of the robot described in the summary.

The procedure leading to the dental restoration is now described in FIG. 3, which shows a simplified view of an operating room of the dental office 84 equipped with an assistance system 5 as described in the summary. The elements of the dental office 84 shown in FIG. 2 are all illustrated in FIG. 3. The room comprises standard technical tools of the practitioner D such as a seat 84A to accommodate the patient P, a station 84B comprising a water supply and a tower carrying a lamp 84C placed high up, and a mobile arm extending around the seat 84A, to which a pallet 84D of standard instruments of the practitioner D is mechanically coupled. The assistance system 5 comprises a robot 6 which is mobile around the seat 84A, in a zone 80R. It is equipped with wheels to ensure its mobility. It is also equipped with a robotic articulated arm 61 which is mobile and attached to a machining tool consisting of a dental drill 62 placed at one end of the robotic arm 61. The assistance system 5 also comprises a spatial guidance system for the robot 6 comprising a detector 73, preferably attached to a lamp support 84C, overhanging the seat 84A. As shown in FIG. 4, the detector 73 is configured to determine:

a first distance separating one of its points of at least one of the first target symbols 74 from a first spatial reference frame 71 attached to the robotic arm 61;

a second distance separating the one of its points from at least one of the second target symbols 77 of a second spatial reference frame 72 which is attached to a point in an operating zone of the dentition 92.

To allow the detector 73 to determine these first and second distances with depth, in any direction in space, two cameras 73A and 73B spaced on the detector 73 are provided. The second spatial reference frame 72 comprises a dental part 75 which is adapted to fit into a portion of the dentition 92 comprised within the operating zone, which portion does not comprise the tooth 91, and a protruding element 76 comprising the second target symbols 77. The dental part 75 and the protruding element are provided with a female-male attachment system 78 which allows a male end of the protruding element 76 to be clipped into a female end of the dental part 75, so that the protruding element 76 can be advantageously reused from one dental operation to the next, while discarding the dental part 75 after use. Preferably, the dental part is made of a solid and inexpensive material from the first computer file 11 to make a partial dental impression that fits perfectly into the portion of the dentition 92. The dental part 75 is, for example, designed by an additive manufacturing process. It is necessary to design the protruding element as extending outside the operating zone to facilitate the visibility of the second target symbols 77 by the detector 73 while ensuring that the second spatial reference frame 72 reports the movements of the patient P relative to a fixed room reference frame and the robotic arm 61. Finally, the spatial guidance system comprises a computer logic unit 52 comprising a processor arranged within a robot housing 6, so as to limit the space requirement of the assistance system 5. The computer logic unit 52 is configured to:

reading the fourth computer file 14, receiving data on the first and second distances from the detector 73, and determining information for comparing the data with the machining instructions of the fourth computer file 14, controlling and/or stopping the robot 6 and/or the dental drill 62 according to the comparison information.

The assistance system 5 also comprises a communication tool 51 digitally connected to the computer unit 52 and comprising a screen to communicate the comparison information to the practitioner D. Thus, and as detailed in the summary of the disclosure, the practitioner D can be guided in his milling by the assistance system 5 in such a way as to guarantee a high degree of reliability and speed of the operation, as well as a high degree of milling precision, and in particular, obtaining a surface of the milled tooth 91 corresponding exactly to the intrados of the crown 1 to be placed. Optionally, the robot 6 comprises another mobile mechanical arm comprising another detector 73' of a structure and for a use similar to the detector 73'. Optionally, the robot 6 comprises another tool 51' of a structure and a use similar to the communication tool 51. In particular, it is digitally connected to the computer unit 52 to communicate and/or receive comparison information to the practitioner D. It preferably consists of one of a laptop computer, or an interactive tablet, for the practitioner D. During the dental surgery operation, the practitioner D acting as an assisted operator is essentially located in a zone 80D, surrounded laterally by the zone 80R.

Figure 10:
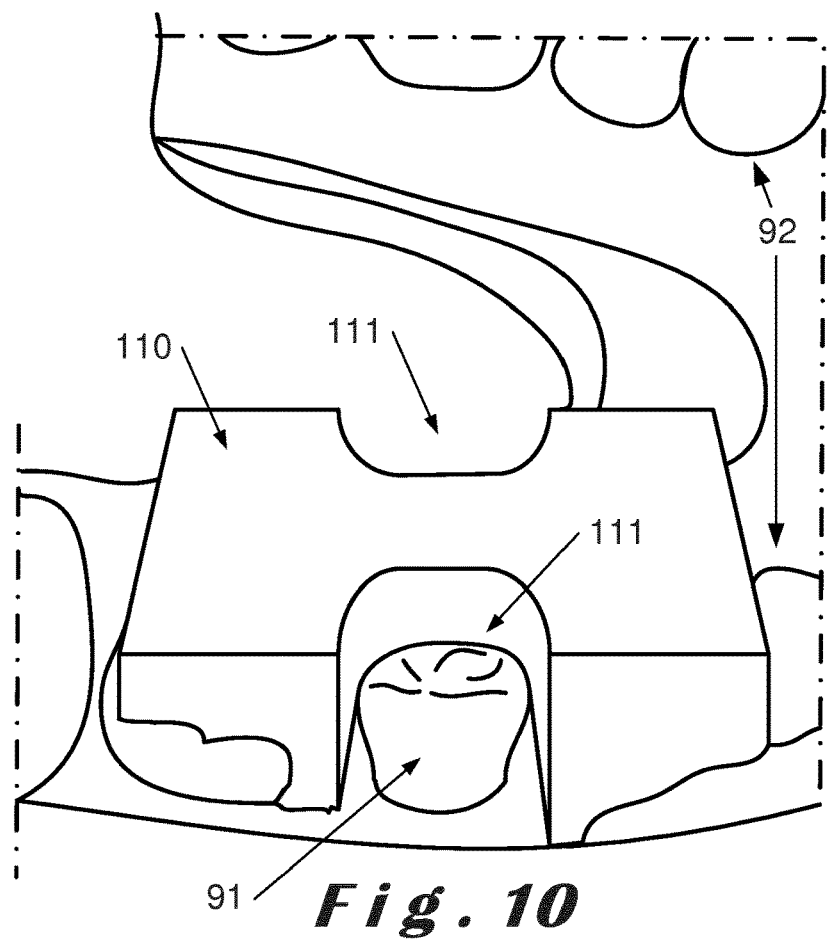
FIG. 10 shows a three-dimensional view of a use of a guide according to the disclosure.

The procedure leading to the dental restoration described in FIGS. 3 and 4 is advantageously (semi-)automated with the aid of the assistance system 5 as described in the summary. However, this assistance system 5 is likely to be expensive and complex to implement. The disclosure therefore proposes inexpensive and very advantageous alternatives for control key and guides for machining the at least one tooth 91. This control key 100 and these guides 110, 120 and 130 are introduced precisely in the summary of the disclosure and illustrated in FIGS. 5 to 10. The control key 100 is formed from a block of rigid raw material which is machined by means of the embodiments of the disclosure, so that the three-dimensional representation of the intrados 1B of the prosthetic element 1 is formed from a lower face of the block. Preferably, three-dimensional representations of the adjacent teeth 91A and 91B are also machined in a similar manner. The control key 100 therefore acts as a mold that can be placed on the dentition 92 of the patient when the at least one tooth 91 has been prepared by a practitioner. The control key 100 thus allows the practitioner to detect any cutting errors in the at least one tooth 91. To facilitate this, the control key 100 is cut into slices 101 parallel to a plane (vertical in the case illustrated, but which can just as easily be horizontal). In this way, the practitioner can move certain slices 101 so that he can observe the evolution of its cutting and its good correspondence with the intrados 1B of the prosthetic element 1. This is shown in particular in FIG. 6. The guides 110, 120 and 130 are for their part directly associated with the practice of machining the at least one tooth 91 with regard to the method comprising the steps (iv.1) to (iv.6) as explained in the summary of the disclosure. They are shown from above (downstream of the insertion axis when arranged on the at least one tooth 91) in FIGS. 7 to 9 and are obtained by applying the first, second and third collections of machining instructions to the first, second and third blocks of a transparent rigid raw material respectively, as explained in the summary of the disclosure. Each comprises a cavity 91' in this raw material corresponding to the isolated three-dimensional representation of the at least one tooth 91 which is obtained by the step (iii.1). Windows 111, 121 and 132 are provided in the guides 110, 120 and 130 respectively to access this cavity 91' according to the directions and angles of attack for the dental cutting adapted to best reproduce certain sub-steps or results resulting from sub-steps of the step (iv). The guide 130 is machined so that two sloping edges 131 are created giving a roof shape to this portion of the block of raw material, the slopes being determined according to an orientation angle of volumetric reduction of the middle zone of the at least one tooth 91 comprised in the dental protocol according to the step (iii). The placement of such a guide 110 during the dental preparation is shown in FIG. 10. These guides 110, 120, 130 guide the machining of the at least one tooth 91 to reproduce in particular the primary surface according to the sub-step (iv.4). Other such guides can be derived from the sub-steps of the step (iv) without departing from the scope of the disclosure.

Figure 12:
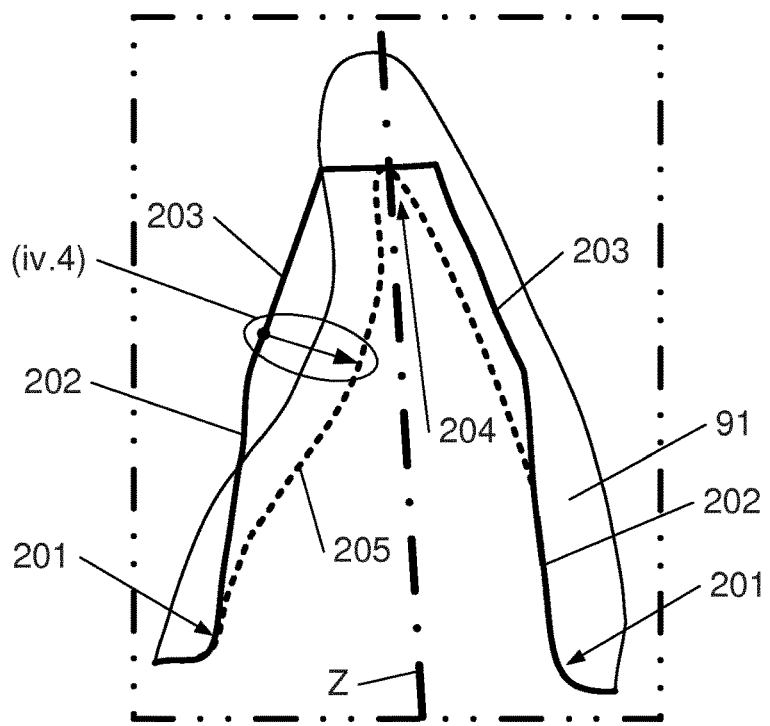
FIG. 12 shows a particular application of the steps (iv.1) to (iv.6) of a design method according to a preferred embodiment of the disclosure.
Figure 11:
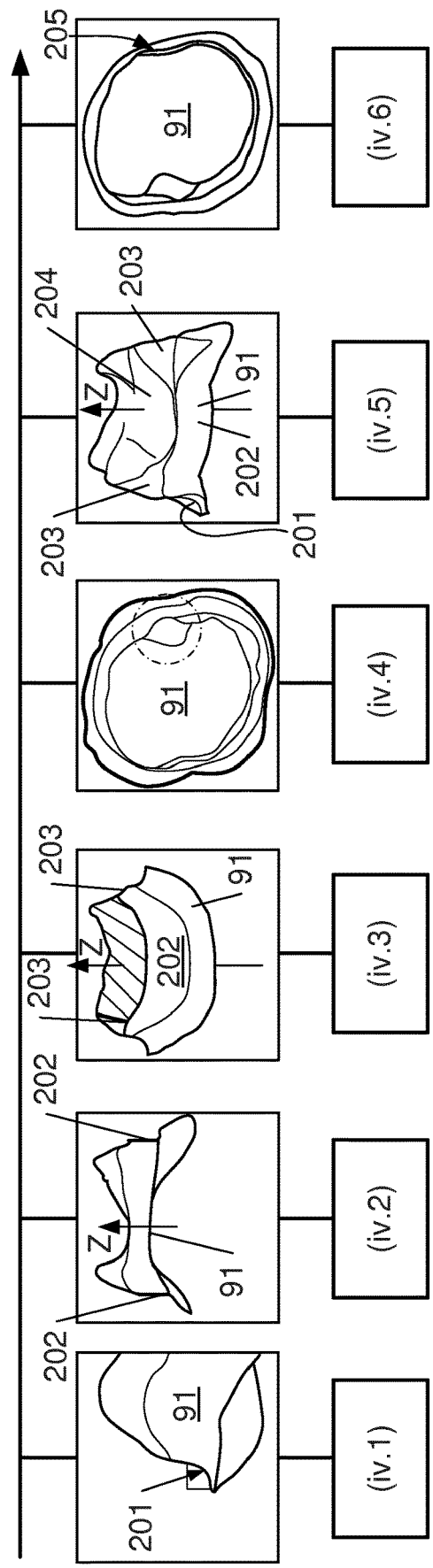
FIG. 11 shows a schematic view of an implementation of the steps (iv.1) to (iv.6) of a method for designing a prosthetic element according to a preferred embodiment of the disclosure.

The decomposition of the step (iv) into the sub-steps (iv.1) to (iv.6) is commented in the summary of the disclosure and illustrated in FIG. 11 with respect to a crown, this choice being not limitative as these sub-steps apply effectively to the case of other prosthetic elements 1, since they influence a choice of insertion axis Z by the dental protocol according to the step (iii.1) to (iii.3). Thus, this figure can be used to illustrate these sub-steps according to the following references. The elliptical fillets 201 are generated in the sub-step (iv.1) at the marginal zone of the at least one tooth 91, the first conical surface 202 (this one being approximately cylindrical) is generated in the step (iv.2) around the marginal zone of the at least one tooth 91, the second conical surface 203 is generated in the step (iv.3) around the middle zone of the at least one tooth 91, the step (iv) allows to compare the conical surfaces 202 and 203 with an offset surface that would be obtained by moving each point of the marginal and middle zones towards the insertion axis Z according to the first offset data from the dental protocol. This is because it is possible for particular teeth that points on the conical surfaces 202 and 203 are outside the (three-dimensional representation of the) at least one tooth 91, so that it would no longer make sense to define a volumetric reduction of the at least one tooth 91 on this basis. This is illustrated in FIG. 12 in particular. It is therefore necessary to project these points into the (three-dimensional representation of the) at least one tooth 91. This projection must be made taking into account that it must "enter far enough" into the (three-dimensional representation of the) at least one tooth 91 to ensure sufficient space for the prosthetic element 1, as this has a certain thickness. It is the great interest of first offset data that comes from the dental protocol and encode sort of a preference this minimum thickness that is necessary to remove on each face of the at least one tooth 91 in order to be able to place the prosthetic element 1 taking into account the tolerances associated with it. Thus the step (iv.4) proposes this advantageous and judicious correction of the conical surfaces 202 and 203 to allow a suitable primary reduction surface to be defined for carrying out the volumetric reduction of the at least one tooth 91. Next, a reduced occlusal surface 204 is generated in the step (iv.5) and finally a final total surface 205 is generated in the step (iv.6), which consists of the assembly of the fillets 201, the smoothed and regularized primary reduction and occlusal surfaces 204.

In summary, the disclosure concerns a method for designing a prosthetic element 1 that can be executed prior to a cutting of a tooth 91 of a patient for the placement of the prosthetic element 1.

The present disclosure has been described in relation to specific embodiments, which are purely illustrative and should not be considered as limiting. In a general manner, it will be obvious to a person skilled in the art that the present disclosure is not limited to the examples illustrated and/or described above. The disclosure comprises each of the new features as well as all their combinations.

The invention claimed is:

1. A computer-implemented method of manufacturing a prosthetic element comprising:
   (i) providing a first computer file comprising:
      an intra-oral three-dimensional representation of a dentition comprising at least one tooth to be restored by means of said prosthetic element; and
      a radiographic image of said dentition; and
   by means of a computer system:
      identifying common reference axes on said intra-oral three-dimensional representation and on said radiographic image; and
      performing a comparison said intra-oral three-dimensional representation with said radiographic image, the comparison comprising an overlay of said common reference axes;
   (ii) determining a three-dimensional representation of an extrados of said prosthetic element on the basis of said first computer file;
   (iii) determining technical parameters comprising at least one of:
      a dental protocol;
      a type of dental preparation; and
      technical constraints,
      on the basis of said first computer file, at least one of said technical parameters being determined on the basis of the comparison of step (i);
   (iv) generating a second computer file comprising a three-dimensional representation of a volumetric reduction of said at least one tooth on the basis of said technical parameters;
   (v) validating and/or modifying said second computer file;
   (vi) obtaining a three-dimensional representation of an intrados of said prosthetic element on the basis of said second validated and/or modified computer file;
   (vii) generating a third computer file comprising information relating to the three-dimensional representations of said extrados and intrados of said prosthetic element;
   (vii') generating a fourth computer file on the basis of said second validated and/or modified computer file, said fourth computer file comprising machining instructions for said at least one tooth corresponding to said three-dimensional representation of said volumetric reduction of said at least one tooth;
   (vii") driving a dental drill along a path with a robotic arm according to the machining instructions of the fourth computer file so that the dental drill mills the surface of the tooth to correspond to the intrados of the prosthetic element; and
   (viii) manufacturing said prosthetic element according to said third computer file,
   wherein steps (ii) to (vii') are implemented by means of said computer system.

2. The computer-implemented method according to claim 1, wherein step (ii) comprises:
   (ii.1) selecting a three-dimensional representation model of a model dentition from a database on the basis of said first computer file;
   (ii.2) selecting a zone of the three-dimensional representation model corresponding to a zone of the intra-oral three-dimensional representation corresponding to said at least one tooth;
   (ii.3) validating and/or modifying the zone of the three-dimensional representation model on the basis of said first computer file; and
   (ii.4) defining the three-dimensional representation of the extrados of said prosthetic element from the validated and/or modified zone of the three-dimensional representation model.

3. The computer-implemented method according to claim 1, wherein step (iii) comprises:
   (iii.1) determining a type of dental preparation on the basis of said first computer file;
   (iii.2) algorithmically generating a dental protocol on the basis of the type of dental preparation determined in sub-step (iii.1),
   said dental protocol consisting of a collection of numerical data to geometrically parameterise said three-dimensional representation of the volumetric reduction; and
   (iii.3) validating and/or modifying said dental protocol on the basis of the comparison of step (i).

4. The computer-implemented method according to claim 1, wherein:
   said second computer file consists of a file of modifiable STL format; and
   step (v) comprises a validation and/or a modification of each of the geometric parameters relating to said three-dimensional representation of the volumetric reduction of said at least one tooth in a set of admissible values previously defined by at least one of said technical parameters determined in step (iii).

5. The computer-implemented method according to claim 1, wherein:
said information of said third computer file comprises instructions for machining a material; and
step (viii) comprises machining said material on the basis of said machining instructions.

6. A set of apparatus for designing a prosthetic element by carrying out the computer-implemented method according to claim 1, the set of apparatus comprising:
at least one imaging apparatus for providing the first computer file of step (i) of the computer-implemented method;
a computer system comprising:
an interface for receiving:
at least one technical parameter determined in step (iii) of the computer-implemented method, and
validations and/or modifications of the second computer file of step (v) of the computer-implemented method;
and to visualise and/or communicate data on:
the intra-oral three-dimensional representation and the radiographic image of the first computer file provided in step (i);
the three-dimensional representation of the extrados of said prosthetic element obtained in step (ii);
the three-dimensional representation of the volumetric reduction of the at least one tooth of the second computer file generated in step (iv);
the three-dimensional representation of the volumetric reduction of the at least one tooth of the second computer file validated and/or modified in step (v); and
the three-dimensional representation of the intrados of said prosthetic element obtained in step (vi); and
a logic unit for at least partially implementing steps (ii), (iv), (vi) and (vii) of the computer-implemented method; and
a production machine for reading the information from the third computer file generated in step (vii), and for implementing step (viii) of the computer-implemented method.

7. A non-transitory computer-readable medium having logic stored thereon that in response to execution by a computer, causes the computer to perform actions comprising steps of:
executing a first set of instructions that implement step (iv) of the computer-implemented method according to claim 1;
executing a second set of instructions that implement step (vii) of the computer-implemented method according to claim 1; and
executing a third set of instructions that implement step (vii') of the computer-implemented method according to claim 1.

8. A computer-readable medium on which is recorded at least one of the sets of instructions according to claim 7.

9. A computer-readable medium on which is recorded:
a third and/or a fourth computer file generated by the computer-implemented method according to claim 1.

10. A prosthetic element produced by the computer-implemented method according to claim 1.

11. A computer-implemented method of manufacturing a prosthetic element comprising:
(i) providing a first computer file comprising:
an intra-oral three-dimensional representation of a dentition comprising at least one tooth to be restored by means of said prosthetic element; and
a radiographic image of said dentition; and
by means of a computer system:
identifying common reference axes on said intra-oral three-dimensional representation and on said radiographic image; and
performing a comparison said intra-oral three-dimensional representation with said radiographic image, the comparison comprising an overlay of said common reference axes;
(ii) determining a three-dimensional representation of an extrados of said prosthetic element on the basis of said first computer file;
(iii) determining technical parameters comprising at least one of:
a dental protocol;
a type of dental preparation; and
technical constraints,
on the basis of said first computer file, at least one of said technical parameters being determined on the basis of the comparison of step (i);
(iv) generating a second computer file comprising a three-dimensional representation of a volumetric reduction of said at least one tooth on the basis of said technical parameters;
(v) validating and/or modifying said second computer file;
(vi) obtaining a three-dimensional representation of an intrados of said prosthetic element on the basis of said second validated and/or modified computer file;
(vii) generating a third computer file comprising information relating to the three-dimensional representations of said extrados and intrados of said prosthetic element;
(vii') driving a dental drill along a path with a robotic arm according to the information of the third computer file so that the dental drill mills the surface of the tooth to correspond to the intrados of the prosthetic element; and
(viii) manufacturing said prosthetic element according to said third computer file,
wherein steps (ii) to (viii) are implemented by means of said computer system,
wherein step (iii) further comprises:
(iii.1) determining a type of dental preparation on the basis of said first computer file;
(iii.2) algorithmically generating a dental protocol on the basis of the type of dental preparation determined in sub-step (iii.1),
said dental protocol consisting of a collection of numerical data to geometrically parameterise said three-dimensional representation of the volumetric reduction; and
(iii.3) validating and/or modifying said dental protocol on the basis of the comparison of step (i), and
wherein sub-step (iii.1) further comprises:
visualizing said intra-oral three-dimensional representation of a dentition;
segmenting said intra-oral three-dimensional representation of a dentition so as to obtain an isolated three-dimensional representation of the at least one tooth;
algorithmically generating vestibular, lingual, mesial, distal and occlusal faces of the at least one tooth by identifying a point on each of these faces at the isolated three-dimensional representation of the at least one tooth;

modifying and/or validating boundaries of said vestibular, lingual, mesial, distal and occlusal faces of the at least one tooth by adding, moving and/or removing points of these faces on the isolated three-dimensional representation of the at least one tooth; and identifying a reference frame of at least one of said reference axes on the basis of the comparison of step (i), the reference frame comprising an insertion axis of the at least one tooth.

12. The computer-implemented method according to claim 11, wherein the numerical data comprise:

for each face among the vestibular, lingual, mesial and distal faces of said at least one tooth:
  a radius; and
  a height,
  corresponding to a parameterisation of a transverse section of an elliptical fillet of the face along an elliptical arc of semi-major axis corresponding to said radius measured essentially perpendicularly to said insertion axis and of semi-minor axis corresponding to said height measured essentially parallel to said insertion axis;

for each of the vestibular, lingual, mesial and distal faces of said at least one tooth,
a first offset data corresponding to a displacement of each point of the face on the isolated three-dimensional representation of the at least one tooth towards the insertion axis;

for the occlusal face of said at least one tooth,
a first offset data corresponding to a displacement of each point of the occlusal face on the isolated three-dimensional representation of the at least one tooth along the insertion axis;

two percentages defining two zones consisting of marginal and middle zones of the at least one tooth on the isolated three-dimensional representation of the at least one tooth, each percentage corresponding to the ratio between a height of one zone and a height of both zones, these heights being measured essentially parallel to the insertion axis; and for each of said zones:
  a volumetric reduction orientation angle measured with respect to the insertion axis; and
  a minimum height.

13. The computer-implemented method according to claim 12, wherein the technical constraints comprise a minimum thickness of a material for the design of the prosthetic element, and in that the first offset data of the faces depend on this minimum thickness.

14. The computer-implemented method according to claim 12, wherein step (iv) comprises an algorithmic generation of a three-dimensional representation of a volumetric reduction of said at least one tooth, comprising:

(iv.1) generating a marginal surface consisting of the elliptical fillets of the vestibular, lingual, mesial and distal faces of said at least one tooth;

(iv.2) generating a first conical surface around said insertion axis (Z) from an end curve bordering the marginal surface generated in sub-step (iv.1), this first conical surface extending parallel to said marginal surface and having an inclination towards the insertion axis of an angle corresponding to the volumetric reduction orientation angle of said marginal zone;

(iv.3) generating a second conical surface around said insertion axis from an end curve bordering the first conical surface generated in sub-step (iv.2), this second conical surface extending parallel to said middle zone and having an inclination towards the insertion axis of an angle corresponding to the orientation angle of volumetric reduction of said middle zone;

(iv.4) calculating a second offset data for each point of the marginal and middle zones on the isolated three-dimensional representation of the at least one tooth, this second offset data corresponding to a displacement of this point towards or away from the insertion axis to displace this point on one of the first or second conical surfaces; and defining a primary reduction surface by moving each point from the marginal and middle zones towards the insertion axis according to:
  the second offset data of this point if it corresponds to a displacement towards the insertion axis and if it is larger than the first offset data of this point, and
  the first offset data of this point otherwise;

(iv.5) generating an occlusal surface from an end curve bordering the primary reduction surface generated in sub-step (iv.4) by a displacement of each point on the occlusal face on the isolated three-dimensional representation of the at least one tooth along the insertion axis according to the first offset data; and (iv.6) smoothing and/or regularising a total surface consisting of the assembly of the marginal, primary reduction and occlusal surfaces, this total surface having a plane tangent to the total surface at an intersection with the insertion axis perpendicular to the insertion axis.

15. The computer-implemented method according to claim 14, further comprising:

(iv') generating a sixth computer file on the basis of said first computer file and said dental protocol validated and/or modified in step (iii.3), the sixth computer file comprising three collections of instructions for machining a rigid raw material, each of these collections comprising machining instructions for creating a cavity in the rigid raw material corresponding to the isolated three-dimensional representation, a first of the collections of instructions further comprising machining instructions for creating an access window at least partially conical around the cavity following the first and second conical surfaces, a second of the collections of instructions further comprising machining instructions for creating two windows of upper access to the cavity bordering mesial and distal faces of the cavity which correspond to the mesial and distal faces of said at least one tooth on the isolated three-dimensional representation, and a third of the collections of instructions further comprising instructions for machining a portion of the rigid raw material surrounding a middle zone of the cavity corresponding to the middle zone of said at least one tooth on the isolated three-dimensional representation, to create two sloping edges according to the orientation angle of volumetric reduction of the middle zone; and (viii') machining a first, a second and a third block of said rigid raw material, respectively, on the basis of the first, second and third collections of machining instructions of said sixth computer file to produce three guides for machining the at least one tooth according to said three-dimensional representation of the volumetric reduction of the at least one tooth.

16. The computer-implemented method according to claim 15, further comprising interlocking at least one safety abutment and a rail for positioning a dental drill on the guides.

17. Machining guides produced by the computer-implemented method according to claim 15.

18. A computer-implemented method of manufacturing a prosthetic element comprising:
  (i) providing a first computer file comprising:
    an intra-oral three-dimensional representation of a dentition comprising at least one tooth to be restored by means of said prosthetic element; and
    a radiographic image of said dentition; and
    by means of a computer:
      identifying common reference axes on said intra-oral three-dimensional representation and on said radiographic image; and
      performing a comparison said intra-oral three-dimensional representation with said radiographic image, the comparison comprising an overlay of said common reference axes;
  (ii) determining a three-dimensional representation of an extrados of said prosthetic element on the basis of said first computer file;
  (iii) determining technical parameters comprising at least one of:
    a dental protocol;
    a type of dental preparation; and
    technical constraints,
    on the basis of said first computer file, at least one of said technical parameters being determined on the basis of the comparison of step (i);
  (iv) generating a second computer file comprising a three-dimensional representation of a volumetric reduction of said at least one tooth on the basis of said technical parameters;
  (v) validating and/or modifying said second computer file;
  (vi) obtaining a three-dimensional representation of an intrados of said prosthetic element on the basis of said second validated and/or modified computer file;
  (vii) generating a third computer file comprising information relating to the three-dimensional representations of said extrados and intrados of said prosthetic element; and
  (viii) manufacturing said prosthetic element according to said third computer file,
  (vii") generating a fifth computer file on the basis of said second validated and/or modified computer file, said fifth computer file comprising information relating to the three-dimensional representation of the intrados of said prosthetic element obtained in step (vi), this information comprising instructions for machining a rigid raw material corresponding to said three-dimensional representation of the intrados of said prosthetic element;
  (vii") driving a dental drill along a path with a robotic arm according to the instructions of the fifth computer file so that the dental drill mills the surface of the tooth to correspond to the intrados of the prosthetic element; and
  (viii") machining a block of said rigid raw material on the basis of the machining instructions of said fifth computer file, so as to produce a control key of a machining of said at least one tooth corresponding to a machining according to said three-dimensional representation of the volumetric reduction of said at least one tooth,
  wherein steps (ii) to (viii") are implemented by means of said computer system.

19. The computer-implemented method according to claim 18, further comprising cutting the control key into slices parallel to a plane.

20. A control key produced by the computer-implemented method according to claim 18.

* * * * *